US011938021B2

(12) United States Patent
Tzadok et al.

(10) Patent No.: US 11,938,021 B2
(45) Date of Patent: *Mar. 26, 2024

(54) COVERED PROSTHETIC HEART VALVE

(71) Applicant: Edwards Lifesciences Corporation, Irvine, CA (US)

(72) Inventors: Sara Tzadok, Or-Akiva (IL); Khen Perlmutter, Binyamina (IL); Darshin S. Patel, San Juan Capistrano, CA (US); Boaz Manash, Givat Ada (IL); Ajay Chadha, Irvine, CA (US); Waina Michelle Chu, Tustin, CA (US); Chambory Chhe, Santa Ana, CA (US); Evan T. Schwartz, Huntington Beach, CA (US); Sandip Vasant Pawar, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 17/456,337

(22) Filed: Nov. 23, 2021

(65) Prior Publication Data

US 2022/0079750 A1 Mar. 17, 2022

Related U.S. Application Data

(63) Continuation of application No. 15/876,053, filed on Jan. 19, 2018, now Pat. No. 11,185,406.
(Continued)

(51) Int. Cl.
*A61F 2/24* (2006.01)
*A61F 2/00* (2006.01)

(52) U.S. Cl.
CPC .......... *A61F 2/2412* (2013.01); *A61F 2/0077* (2013.01); *A61F 2/2409* (2013.01);
(Continued)

(58) Field of Classification Search
CPC .... A61F 2/2418; A61F 2/2412; A61F 2/2409; A61F 2/07; A61F 2/2475; A61F 2/06;
(Continued)

(56) References Cited

U.S. PATENT DOCUMENTS 30,912 A 12/1860 Hancock
3,409,013 A 11/1968 Berry
(Continued)

FOREIGN PATENT DOCUMENTS

DE 0144167 C 9/1903
DE 2246526 A1 3/1973
(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.
(Continued)

*Primary Examiner* — Seema Mathew
(74) *Attorney, Agent, or Firm* — Carsten C. Grellmann; Klarquist Sparkman, LLP

(57) ABSTRACT

A prosthetic heart valve has a frame including a plurality of strut members, an inflow end, and an outflow end. A leaflet structure is situated at least partially within the frame, and a covering is disposed around an exterior of the frame. The covering includes a cushioning layer, and a first strip member folded over an inflow circumferential edge portion of the cushioning layer to form a first protective portion. A second strip member is folded over an outflow circumferential edge portion of the cushioning layer to form a second protective portion. The first strip member and the second strip member are spaced apart from each other along a longitudinal axis of the prosthetic heart valve.

20 Claims, 29 Drawing Sheets

Related U.S. Application Data

(60) Provisional application No. 62/535,724, filed on Jul. 21, 2017, provisional application No. 62/520,703, filed on Jun. 16, 2017, provisional application No. 62/449,320, filed on Jan. 23, 2017.

(52) U.S. Cl.
CPC .... *A61F 2/2418* (2013.01); *A61F 2002/0086* (2013.01); *A61F 2/243* (2013.01); *A61F 2210/0076* (2013.01)

(58) Field of Classification Search
CPC .... A61F 2/246; A61F 2/24; A61F 2/90; A61F 2210/0061; A61F 2210/0076; A61F 2250/0069; A61F 2002/072
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,744,060 A * | 7/1973 | Bellhouse ............ A61F 2/2412 137/849 |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,666,442 A * | 5/1987 | Arru ............ A61F 2/2409 623/2.13 |
| 4,692,164 A | 9/1987 | Dzemeshkevich et al. |
| 4,705,516 A * | 11/1987 | Barone ............ A61F 2/2409 623/2.39 |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,790,843 A | 12/1988 | Carpentier et al. |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A * | 1/1999 | Bessler ............ A61F 2/2418 623/2.38 |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |

(56) References Cited

U.S. PATENT DOCUMENTS

| | | |
|---|---|---|
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,797,002 B2 | 9/2004 | Spence et al. |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,096,554 B2 | 8/2006 | Austin et al. |
| 7,101,395 B2 | 9/2006 | Tremulis et al. |
| 7,125,421 B2 | 10/2006 | Tremulis et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,445,632 B2 | 11/2008 | McGuckin, Jr. et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,637,946 B2 | 12/2009 | Solem et al. |
| 7,655,034 B2 | 2/2010 | Mitchell et al. |
| 7,708,775 B2 | 5/2010 | Rowe et al. |
| 7,737,060 B2 | 6/2010 | Strickler et al. |
| 7,785,366 B2 | 8/2010 | Maurer et al. |
| 7,951,195 B2 | 5/2011 | Antonsson et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,142,492 B2 | 3/2012 | Forster et al. |
| 8,167,932 B2 | 5/2012 | Bourang et al. |
| 8,236,049 B2 | 8/2012 | Rowe et al. |
| 8,291,570 B2 | 10/2012 | Eidenschink et al. |
| 8,323,335 B2 | 12/2012 | Rowe et al. |
| 8,348,998 B2 | 1/2013 | Pintor et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,747,463 B2 | 6/2014 | Fogarty et al. |
| 8,801,776 B2 | 8/2014 | House et al. |
| 9,078,747 B2 | 7/2015 | Conklin |
| 9,078,781 B2 | 7/2015 | Ryan et al. |
| 9,095,434 B2 | 8/2015 | Rowe |
| 9,119,718 B2 | 9/2015 | Keranen |
| 9,192,471 B2 | 11/2015 | Bolling |
| 9,220,594 B2 * | 12/2015 | Braido .................. A61F 2/2436 |
| 9,237,886 B2 | 1/2016 | Seguin et al. |
| 9,314,335 B2 | 4/2016 | Konno |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,610,157 B2 * | 4/2017 | Braido .................. A61F 2/2418 |
| 9,622,863 B2 | 4/2017 | Karapetian et al. |
| 10,201,416 B2 * | 2/2019 | Backus ................. A61F 2/2436 |
| 10,413,401 B2 | 9/2019 | Eberhardt et al. |
| 10,716,664 B2 | 7/2020 | Ratz et al. |
| 10,888,420 B2 * | 1/2021 | Bateman ............... A61F 2/2439 |
| 10,945,836 B2 * | 3/2021 | Braido .................. A61F 2/2418 |
| 10,980,636 B2 * | 4/2021 | Delaloye ............... A61F 2/2454 |
| 11,439,732 B2 * | 9/2022 | Adamek-Bowers ........................ A61F 2/2418 |
| 11,534,294 B2 * | 12/2022 | Braido .................. A61F 2/2433 |
| 2001/0021872 A1 | 9/2001 | Bailey et al. |
| 2002/0026094 A1 | 2/2002 | Roth |
| 2002/0032481 A1 | 3/2002 | Gabbay |
| 2002/0107535 A1 | 8/2002 | Wei et al. |
| 2002/0138135 A1 | 9/2002 | Duerig et al. |
| 2002/0143390 A1 | 10/2002 | Ishii |
| 2002/0151970 A1 | 10/2002 | Garrison et al. |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0171805 A1 * | 9/2003 | Berg ..................... A61F 2/2418 623/2.14 |
| 2003/0212454 A1 | 11/2003 | Scott et al. |
| 2003/0225420 A1 | 12/2003 | Wardle |
| 2004/0024452 A1 | 2/2004 | Kruse et al. |
| 2004/0039436 A1 * | 2/2004 | Spenser ................. A61F 2/243 623/2.14 |
| 2004/0078074 A1 | 4/2004 | Anderson et al. |
| 2004/0111006 A1 | 6/2004 | Alferness et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0273155 A1 * | 12/2005 | Bahler ..................... A61F 2/07 623/1.13 |
| 2006/0004469 A1 | 1/2006 | Sokel |
| 2006/0025857 A1 * | 2/2006 | Bergheim ............... A61L 27/50 623/2.18 |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0195134 A1 | 8/2006 | Crittenden |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |

(56) References Cited

U.S. PATENT DOCUMENTS

| | | |
|---|---|---|
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2007/0293808 A1 | 12/2007 | Williams et al. |
| 2008/0021546 A1 | 1/2008 | Patz et al. |
| 2008/0033542 A1 | 2/2008 | Antonsson et al. |
| 2008/0077235 A1 | 3/2008 | Kirson |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0208330 A1 | 8/2008 | Keranen |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0082845 A1 | 3/2009 | Chobotov |
| 2009/0118826 A1 | 5/2009 | Khaghani |
| 2009/0125118 A1 | 5/2009 | Gong |
| 2009/0157175 A1 | 6/2009 | Benichou |
| 2009/0192601 A1 | 7/2009 | Rafiee et al. |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0036484 A1 | 2/2010 | Hariton et al. |
| 2010/0049313 A1 | 2/2010 | Alon et al. |
| 2010/0082094 A1 | 4/2010 | Quadri et al. |
| 2010/0145440 A1 | 6/2010 | Keranen |
| 2010/0168839 A1* | 7/2010 | Braido ............... A61L 27/3604 |
| | | 623/2.18 |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2010/0312333 A1 | 12/2010 | Navia et al. |
| 2010/0318184 A1 | 12/2010 | Spence |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0098802 A1* | 4/2011 | Braido ............... A61F 2/2409 |
| | | 623/2.11 |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0059458 A1 | 3/2012 | Buchbinder et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2012/0283820 A1 | 11/2012 | Tseng et al. |
| 2012/0296418 A1* | 11/2012 | Bonyuet ............... A61F 2/2415 |
| | | 623/2.18 |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0190862 A1 | 7/2013 | Pintor et al. |
| 2013/0190865 A1 | 7/2013 | Anderson |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0074299 A1 | 3/2014 | Endou et al. |
| 2014/0081394 A1 | 3/2014 | Keranen et al. |
| 2014/0172070 A1 | 6/2014 | Seguin |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277423 A1* | 9/2014 | Alkhatib ............... A61F 2/2436 |
| | | 623/2.38 |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0073545 A1* | 3/2015 | Braido ............... A61F 2/2418 |
| | | 623/2.18 |
| 2015/0073546 A1 | 3/2015 | Braido |
| 2015/0135506 A1 | 5/2015 | White |
| 2015/0148893 A1* | 5/2015 | Braido ............... D05B 1/12 |
| | | 623/2.4 |
| 2015/0157455 A1 | 6/2015 | Hoang et al. |
| 2015/0190227 A1 | 7/2015 | Johnson et al. |
| 2015/0209136 A1* | 7/2015 | Braido ............... A61F 2/2418 |
| | | 623/2.18 |
| 2015/0209141 A1* | 7/2015 | Braido ............... A61F 2/2418 |
| | | 623/2.17 |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0199183 A1* | 7/2016 | Braido ............... A61F 2/2409 |
| | | 623/2.18 |
| 2016/0250022 A1* | 9/2016 | Braido ............... A61F 2/2418 |
| | | 623/2.38 |
| 2016/0256276 A1 | 9/2016 | Yaron |
| 2016/0317305 A1 | 11/2016 | Pelled et al. |
| 2016/0338823 A1* | 11/2016 | Akingba ............... A61F 2/848 |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0014229 A1* | 1/2017 | Nguyen-Thien-Nhon ............... |
| | | A61F 2/2418 |
| 2017/0189174 A1* | 7/2017 | Braido ............... A61F 2/2436 |
| 2017/0217385 A1 | 8/2017 | Rinkleff et al. |
| 2017/0231761 A1* | 8/2017 | Cohen-Tzemach ............... |
| | | A61F 2/2418 |
| | | 623/2.18 |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2018/0000580 A1 | 1/2018 | Wallace et al. |
| 2018/0028310 A1 | 2/2018 | Gurovich et al. |
| 2018/0085217 A1 | 3/2018 | Lashinski et al. |
| 2018/0153689 A1 | 6/2018 | Maimon et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2018/0325665 A1 | 11/2018 | Gurovich et al. |
| 2018/0344456 A1 | 12/2018 | Barash et al. |
| 2019/0091013 A1* | 3/2019 | Alkhatib ............... A61F 2/2433 |
| 2019/0105154 A1* | 4/2019 | Cohen-Tzemach ............... |
| | | A61F 2/2418 |
| 2019/0262507 A1* | 8/2019 | Adamek-Bowers ............... |
| | | A61F 2/2418 |
| 2020/0069415 A1* | 3/2020 | Bialas ............... A61F 2/2415 |
| 2020/0188098 A1* | 6/2020 | Alkhatib ............... A61F 2/2418 |
| 2021/0000596 A1 | 1/2021 | Rajagopal et al. |

(56) References Cited

U.S. PATENT DOCUMENTS

| | | | |
|---|---|---|---|
| 2021/0085453 A1 | 3/2021 | Clague et al. | |
| 2021/0353408 A1* | 11/2021 | Chen | A61F 2/2418 |
| 2022/0338981 A1* | 10/2022 | Alkhatib | A61F 2/2418 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0592410 B1 | 10/1995 |
| EP | 0850607 A1 | 7/1998 |
| EP | 1057460 A1 | 12/2000 |
| EP | 1088529 A2 | 4/2001 |
| EP | 1432369 A1 | 6/2004 |
| EP | 1521550 A2 | 4/2005 |
| EP | 1570809 A1 | 9/2005 |
| EP | 1296618 B1 | 1/2008 |
| EP | 1753374 A4 | 2/2010 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2788217 A1 | 7/2000 |
| FR | 2815844 A1 | 5/2002 |
| GB | 2056023 A | 3/1981 |
| JP | 2003531678 A | 10/2003 |
| JP | 2010517638 A | 5/2010 |
| JP | 2010521226 A | 6/2010 |
| JP | 2014509210 A | 4/2014 |
| JP | 2016538949 A | 12/2016 |
| JP | 2017515643 A | 6/2017 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03028558 A2 | 4/2003 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006011127 A2 | 2/2006 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A3 | 3/2007 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009155561 A2 | 12/2009 |
| WO | 2010011699 A2 | 1/2010 |
| WO | 2010121076 A2 | 10/2010 |
| WO | 2012063228 A1 | 5/2012 |
| WO | 2012162228 A1 | 11/2012 |
| WO | 2013106585 A1 | 7/2013 |
| WO | 2013110722 A2 | 8/2013 |
| WO | 2013114214 A2 | 8/2013 |
| WO | 2014121275 A1 | 8/2014 |
| WO | 2014164832 A1 | 10/2014 |
| WO | WO-2014164832 A1 * | 10/2014 ............ A61F 2/2409 |
| WO | 2015023579 A1 | 2/2015 |
| WO | 2015023862 A2 | 2/2015 |
| WO | 2015085218 A1 | 6/2015 |
| WO | 2015127264 A1 | 8/2015 |
| WO | 2015175302 A1 | 11/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017011697 A1 | 1/2017 |
| WO | 2017103833 A1 | 6/2017 |
| WO | 2018222799 A1 | 12/2018 |
| WO | 2019032992 A2 | 2/2019 |

OTHER PUBLICATIONS

Bailey, S. "Percutaneous Expandable Prosthetic Valves," Textbook of Interventional Cardiology vol. 2, 2nd Ed. pp. 1268-1276. 1994.
H.R. Andersen "History of Percutaneous Aortic Valve Prosthesis," Herz No. 34. pp. 343-346. 2009.
H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Uchida, "Modifications of Gianturco Expandable Wire Stents," American Journal of Roentgenology, vol. 150. pp. 1185-1187. 1986.
Wheatley, "Valve Prostheses," Operalive Surgery, 4th ed. pp. 415-424. 1986.

* cited by examiner

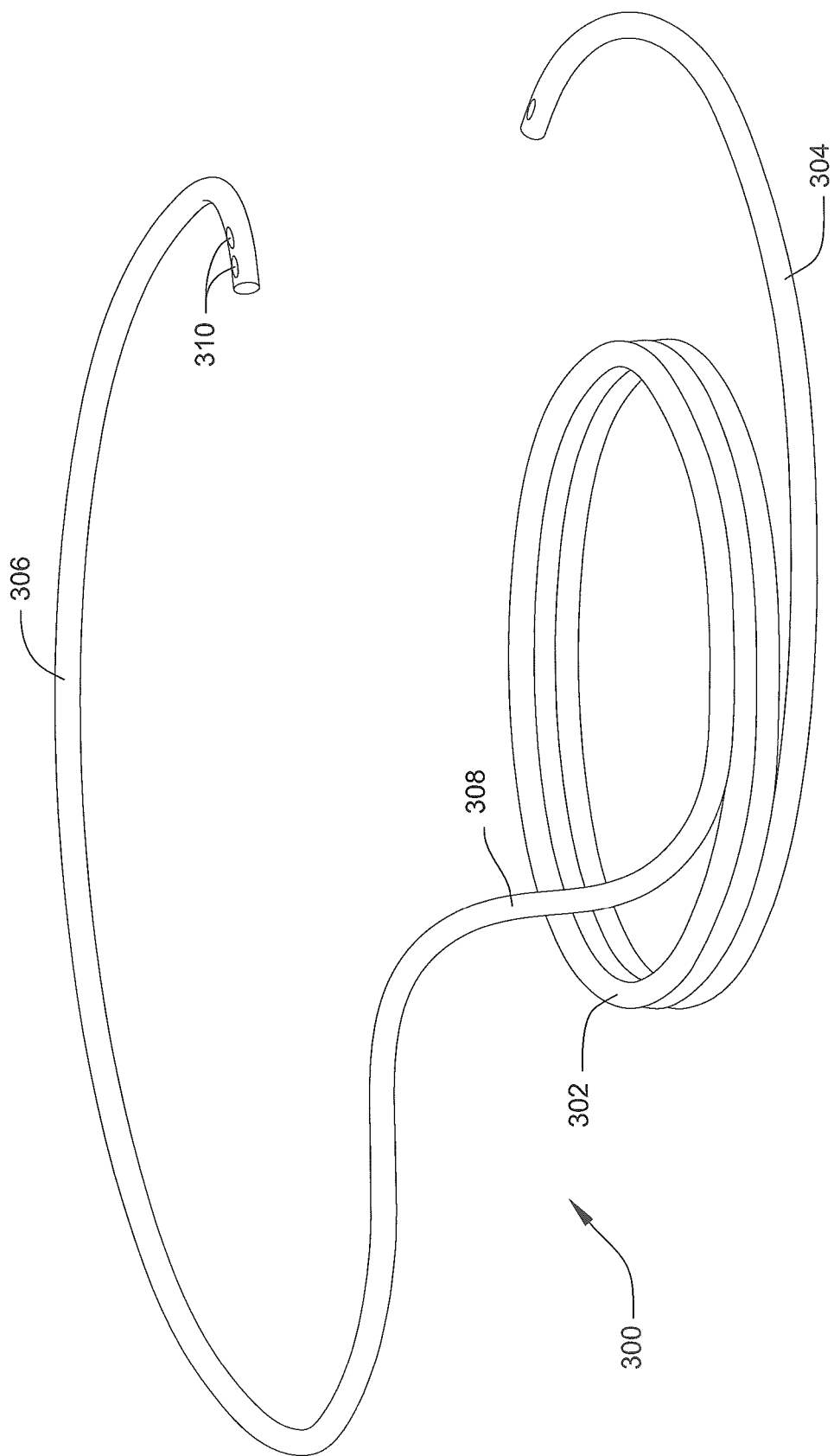

COVERED PROSTHETIC HEART VALVE

CROSS REFERENCE TO RELATED APPLICATIONS

This application is a continuation of U.S. application Ser. No. 15/876,053, filed Jan. 19, 2018, which claims the benefit of U.S. Provisional Patent Application No. 62/535,724 filed on Jul. 21, 2017, U.S. Provisional Patent Application No. 62/520,703 filed on Jun. 16, 2017, and U.S. Provisional Patent Application No. 62/449,320 filed on Jan. 23, 2017. Each of U.S. application Ser. No. 15/876,053, U.S. Provisional Patent Application No. 62/535,724, U.S. Provisional Patent Application No. 62/520,703, and U.S. Provisional Patent Application No. 62/449,320 are incorporated herein by reference in their entirety.

FIELD

The present disclosure relates to prosthetic heart valves, and in particular to prosthetic heart valves including a covering that cushions the tissue of a native heart valve in contact with the prosthetic heart valve.

BACKGROUND

In a procedure to implant a transcatheter prosthetic heart valve, the prosthetic heart valve is typically positioned in the annulus of a native heart valve and expanded or allowed to expand to its functional size. In order to retain the prosthetic heart valve at the desired location, the prosthetic heart valve may be larger than the diameter of the native valve annulus such that it applies force to the surrounding tissue in order to prevent the prosthetic heart valve from becoming dislodged. In other configurations, the prosthetic heart valve may be expanded within a support structure that is located within the native annulus and configured to retain the prosthetic heart valve at a selected position with respect to the annulus. Over time, relative motion of the prosthetic heart valve and tissue of the native heart valve (e.g., native valve leaflets, chordae tendineae, etc.) in contact with the prosthetic heart valve may cause damage to the tissue. Accordingly, there is a need for improvements to prosthetic heart valves.

SUMMARY

Certain disclosed embodiments concern coverings for prosthetic heart valves and methods of making and using the same. In a representative embodiment, a prosthetic heart valve comprises a frame comprising a plurality of strut members, and having an inflow end and an outflow end. The prosthetic heart valve further comprises a leaflet structure situated at least partially within the frame, and a covering disposed around the frame. The covering comprises a first layer and a second layer, wherein the second layer has a plush surface. The first layer is folded over a circumferential edge portion of the second layer to form a protective portion that extends beyond the strut members in a direction along a longitudinal axis of the prosthetic heart valve.

In some embodiments, the protective portion is a first protective portion located adjacent the inflow end of the frame, and the covering further comprises a second protective portion located adjacent the outflow end of the frame.

In some embodiments, the first layer extends along an interior surface of the second layer from the inflow end of the frame to the outflow end of the frame and is folded over a circumferential edge of the second layer at the outflow end of the frame to form the second protective portion.

In some embodiments, the first layer of the first protective portion is configured as a strip member that is folded over the circumferential edge portion of the second layer at the inflow end of the frame.

In some embodiments, a first layer of the second protective portion is configured as a strip member that is folded over a circumferential edge portion of the second layer at the outflow end of the frame.

In some embodiments, the strip member of the first protective portion encapsulates respective apices of the strut members at the inflow end of the frame, and the strip member of the second protective portion encapsulates respective apices of the strut members at the outflow end of the frame.

In some embodiments, the second layer comprises a fabric having a woven layer and a plush pile layer including a plurality of pile yarns.

In some embodiments, the pile yarns are arranged to form a looped pile, or cut to form a cut pile.

In some embodiments, the first layer comprises a tissue layer.

In another representative embodiment, a method comprises securing a first layer to a first surface of a second layer such that a longitudinal edge portion of the first layer extends beyond a longitudinal edge portion of the second layer, the first surface of the second layer being a plush second surface. The method further comprises securing the attached first and second layers into a cylindrical shape to form a covering, and situating the covering about a frame of a prosthetic heart valve, the frame comprising a plurality of strut members. The method further comprises folding the longitudinal edge portion of the first layer over the longitudinal edge portion of the second layer to form a protective portion such that the protective portion extends beyond apices of the strut members in a direction along a longitudinal axis of the valve.

In some embodiments, situating the covering about the frame further comprises situating the covering about the frame such that the plush first surface of the second layer is oriented radially outward.

In some embodiments, the protective portion is an inflow protective portion adjacent an inflow end of the frame, the first layer of the inflow protective portion is configured as a first strip member, and the method further comprises folding a longitudinal edge portion of a second strip member over a longitudinal edge portion of the second layer to form an outflow protective portion adjacent an outflow end of the frame.

In some embodiments, folding the longitudinal edge portion of the first strip member further comprises folding the longitudinal edge portion of the first strip member such that the inflow protective portion encapsulates respective apices of the strut members at the inflow end of the frame, and folding the longitudinal edge portion of the second strip member further comprises folding the longitudinal edge portion of the second strip member such that the outflow protective portion encapsulates respective apices of the strut members at the outflow end of the frame.

In some embodiments, the second layer comprises a fabric having a woven layer and a plush pile layer including a plurality of pile yarns that form the second surface.

In another representative embodiment, a method comprises positioning a prosthetic heart valve in an annulus of a native heart valve. The prosthetic heart valve is in a radially compressed state, and has a frame including a plurality of strut members and having an inflow end and an outflow end. The prosthetic heart valve further comprises a leaflet structure situated at least partially within the frame, and a covering disposed around the frame. The covering comprises a first layer and a second layer. The second layer has a plush surface, and the first layer is folded over a circumferential edge portion of the second layer to form a protective portion that extends beyond the strut members in a direction along a longitudinal axis of the prosthetic heart valve. The method further comprises expanding the prosthetic heart valve in the annulus of the native heart valve such that the leaflet structure of the prosthetic heart valve regulates blood flow through the annulus.

In some embodiments, expanding the prosthetic heart valve further comprises expanding the prosthetic heart valve such that the protective portion prevents tissue of the native heart in contact with the protective portion from contacting apices of the strut members.

In some embodiments, expanding the prosthetic heart valve further comprises expanding the prosthetic heart valve such that leaflets of the native heart valve are captured between the plush surface of the second layer and an anchoring device positioned in the heart.

In some embodiments, the protective portion is a first protective portion located adjacent the inflow end of the frame, and the covering further comprises a second protective portion located adjacent the outflow end of the frame.

In some embodiments, the second layer comprises a fabric having a woven layer and a plush pile layer including a plurality of pile yarns that form the plush surface.

In some embodiments, the first layer is folded over the circumferential edge portion of the second layer such that the protective portion encapsulates respective apices of the strut members.

The foregoing and other objects, features, and advantages of the disclosed technology will become more apparent from the following detailed description, which proceeds with reference to the accompanying figures.

BRIEF DESCRIPTION OF THE DRAWINGS

FIG. 4C is a perspective view of a representative embodiment of a helical anchor.

FIGS. 29-31A are perspective views illustrating a representative method of making the covering of FIG. 27.

DETAILED DESCRIPTION

The present disclosure concerns embodiments of implantable prosthetic heart valves and methods of making and using such devices. In one aspect, a prosthetic heart valve includes an outer covering having a backing layer and a main cushioning layer disposed on the backing layer such that the cushioning layer is oriented radially outward about the circumference of the valve. The cushioning layer can be soft and compliant in order to reduce damage to native tissues of the heart valve and/or of the surrounding anatomy at the implantation site due to, for example, relative movement or friction between the prosthetic valve and the tissue as the heart expands and contracts. The covering can also include an inflow protective portion and an outflow protective portion to cushion the surrounding anatomy and prevent the native tissue of the heart valve from contacting the apices of the strut members of the frame, thereby protecting the surrounding tissue. In another embodiment, the covering can include an inflow strip member and an outflow strip member secured to the cushioning layer and folded over the apices of the strut members to form the inflow and outflow protective portions.

Figure 1:
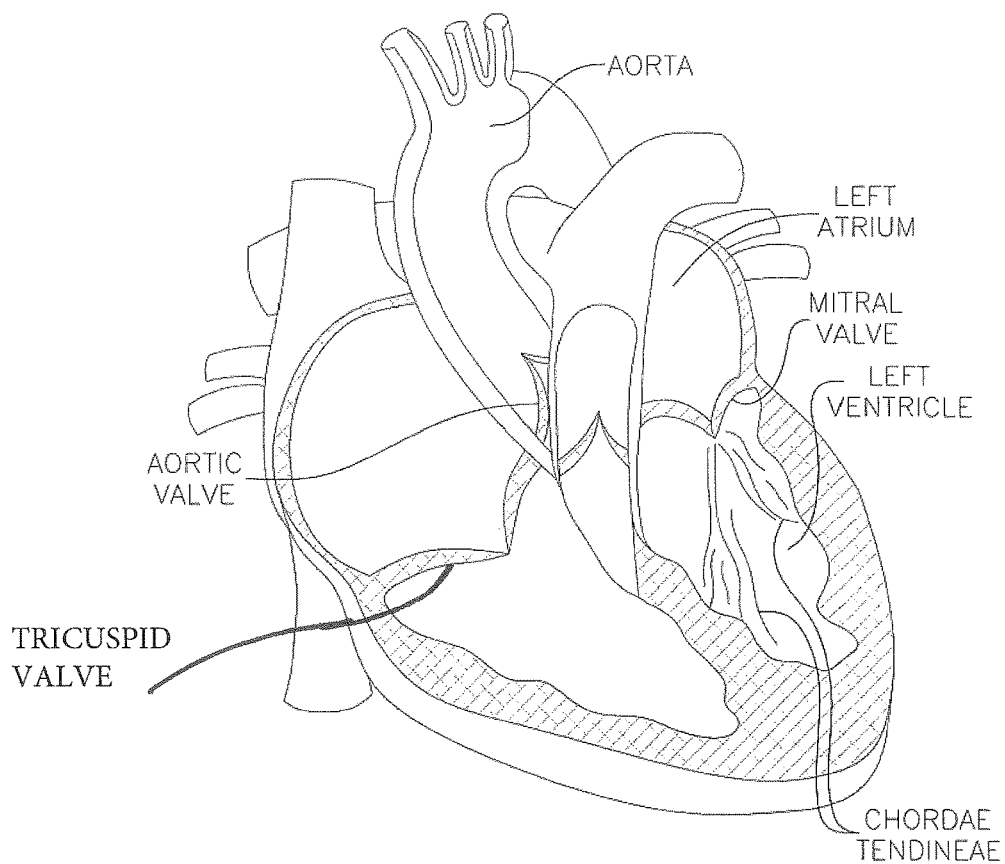
FIG. 1 shows a schematic cross-sectional view of a human heart.
Figure 2:
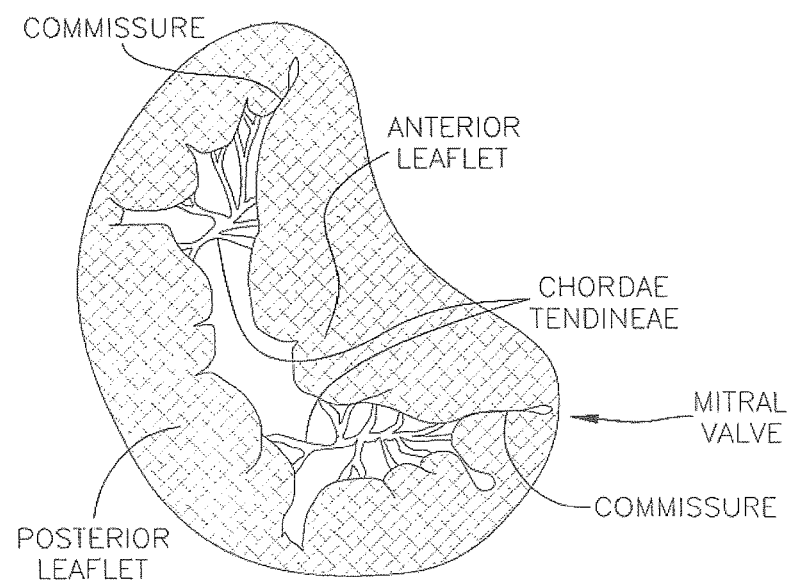
FIG. 2 shows a schematic top view of a mitral valve annulus of a heart.

Embodiments of the disclosed technology can be used in combination with various prosthetic heart valves configured for implantation at various locations within the heart. A representative example is a prosthetic heart valve for replacing the function of the native mitral valve. FIGS. 1 and 2 illustrate the mitral valve of the human heart. The mitral valve controls the flow of blood between the left atrium and the left ventricle. After the left atrium receives oxygenated blood from the lungs via the pulmonary veins, the mitral valve permits the flow of the oxygenated blood from the left atrium into the left ventricle. When the left ventricle contracts, the oxygenated blood that was held in the left ventricle is delivered through the aortic valve and the aorta to the rest of the body. Meanwhile, the mitral valve closes during ventricular contraction to prevent any blood from flowing back into the left atrium.

When the left ventricle contracts, the blood pressure in the left ventricle increases substantially, which urges the mitral valve closed. Due to the large pressure differential between the left ventricle and the left atrium during this time, a possibility of prolapse, or eversion of the leaflets of the mitral valve back into the atrium, arises. A series of chordae tendineae therefore connect the leaflets of the mitral valve to papillary muscles located on the walls of the left ventricle, where both the chordae tendineae and the papillary muscles are tensioned during ventricular contraction to hold the leaflets in the closed position and to prevent them from extending back towards the left atrium. This generally prevents backflow of oxygenated blood back into the left atrium. The chordae tendineae are schematically illustrated in both the heart cross-section of FIG. 1 and the top view of the mitral valve of FIG. 2.

A general shape of the mitral valve and its leaflets as viewed from the left atrium is shown in FIG. 2. Various complications of the mitral valve can potentially cause fatal heart failure. One form of valvular heart disease is mitral valve leak or mitral regurgitation, characterized by abnormal leaking of blood from the left ventricle through the mitral valve back into the left atrium. This can be caused by, for example, dilation of the left ventricle, which can cause incomplete coaptation of the native mitral leaflets resulting in leakage through the valve. Mitral valve regurgitation can also be caused by damage to the native leaflets. In these circumstances, it may be desirable to repair the mitral valve, or to replace the functionality of the mitral valve with that of a prosthetic heart valve, such as a transcatheter heart valve.

Figure 3:
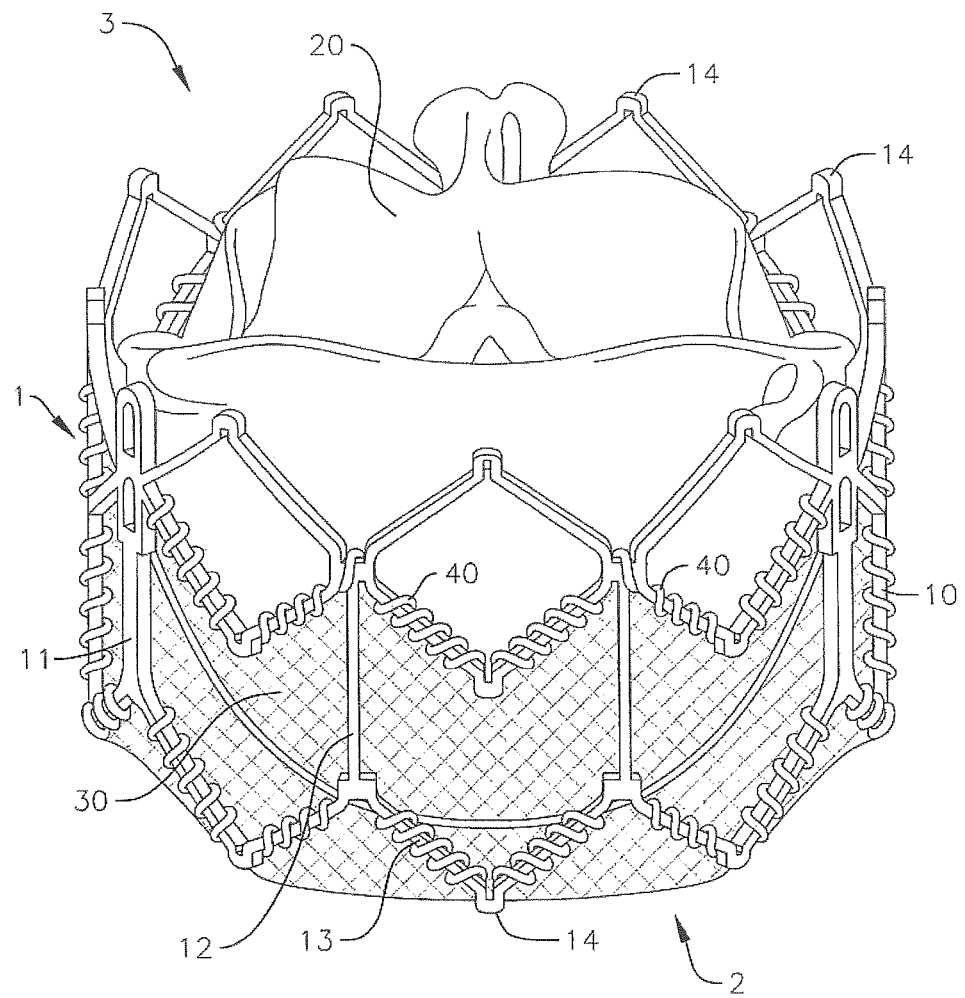
FIG. 3 is a perspective view of an embodiment of a prosthetic heart valve.

Some transcatheter heart valves are designed to be radially crimped or compressed to facilitate endovascular delivery to an implant site at a patient's heart. Once positioned at a native valve annulus, the replacement valve is then expanded to an operational state, for example, by an expansion balloon, such that a leaflet structure of the prosthetic heart valve regulates blood flow through the native valve annulus. In other cases, the prosthetic valve can be mechanically expanded or radially self-expand from a compressed delivery state to the operational state under its own resiliency when released from a delivery sheath. One embodiment of a prosthetic heart valve is illustrated in FIG. 3. A transcatheter heart valve with a valve profile similar to the prosthetic valve shown in FIG. 3 is the Edwards Lifesciences SAPIEN XT™ valve. The prosthetic valve 1 in FIG. 3 has an inflow end 2 and an outflow end 3, includes a frame or stent 10, and a leaflet structure 20 supported inside the frame 10. In some embodiments, a skirt 30 can be attached to an inner surface of the frame 10 to form a more suitable attachment surface for the valve leaflets of the leaflet structure 20.

The frame 10 can be made of any body-compatible expandable material that permits both crimping to a radially collapsed state and expansion back to the expanded functional state illustrated in FIG. 3. For example, in embodiments where the prosthetic valve is a self-expandable prosthetic valve that expands to its functional size under its own resiliency, the frame 10 can be made of Nitinol or another self-expanding material. In other embodiments, the prosthetic valve can be a plastically expandable valve that is expanded to its functional size by a balloon or another expansion device, in which case the frame can be made of a plastically expandable material, such as stainless steel or a cobalt chromium alloy. Other suitable materials can also be used.

The frame 10 can comprise an annular structure having a plurality of vertically extending commissure attachment posts 11, which attach and help shape the leaflet structure 20 therein. Additional vertical posts or strut members 12, along with circumferentially extending strut members 13, help form the rest of the frame 10. The strut members 13 of the frame 10 zig-zag and form edged crown portions or apices 14 at the inflow and outflow ends 2, 3 of the valve 1. Furthermore, the attachment posts 11 can also form edges at one or both ends of the frame 10.

In prosthetic valve 1, the skirt 30 is attached to an inner surface of the valve frame 10 via one or more threads 40, which generally wrap around to the outside of various struts 11, 12, 13 of the frame 10, as needed. The skirt 30 provides a more substantive attachment surface for portions of the leaflet structure 20 positioned closer to the inflow end 2 of the valve 1.

Figure 4A:
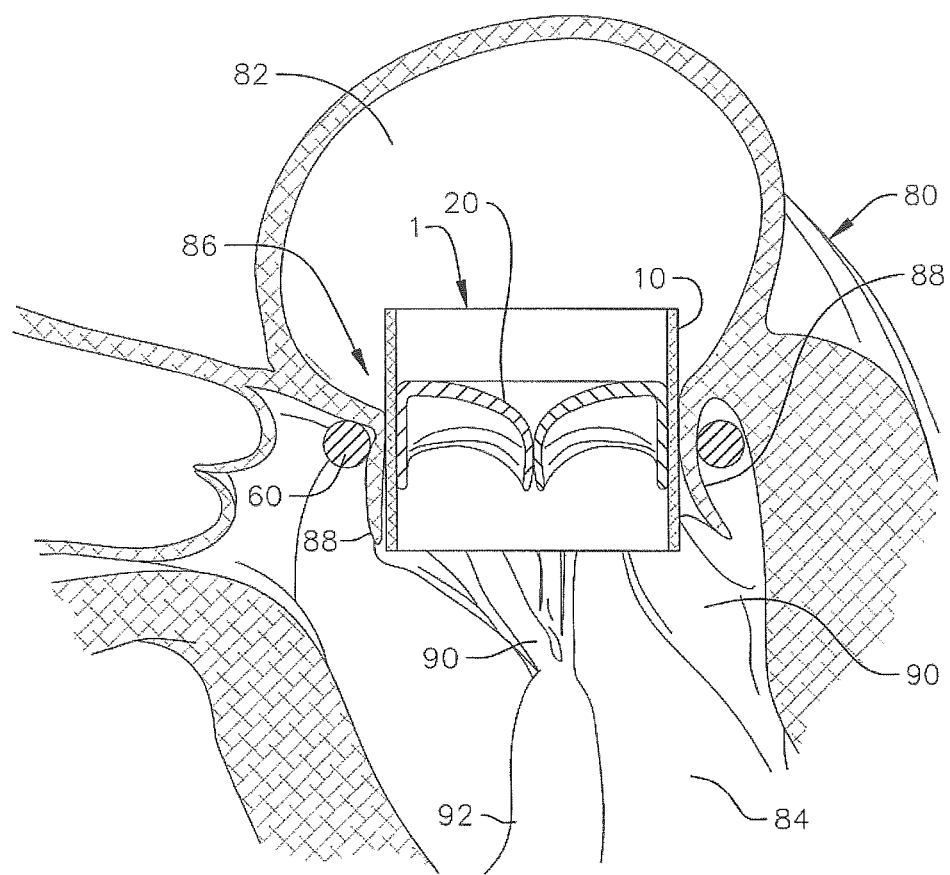
FIG. 4A is a cross-sectional side view of a ring anchor deployed in a mitral position of the heart, with an implanted valve prosthesis, according to one embodiment.
Figure 4B:
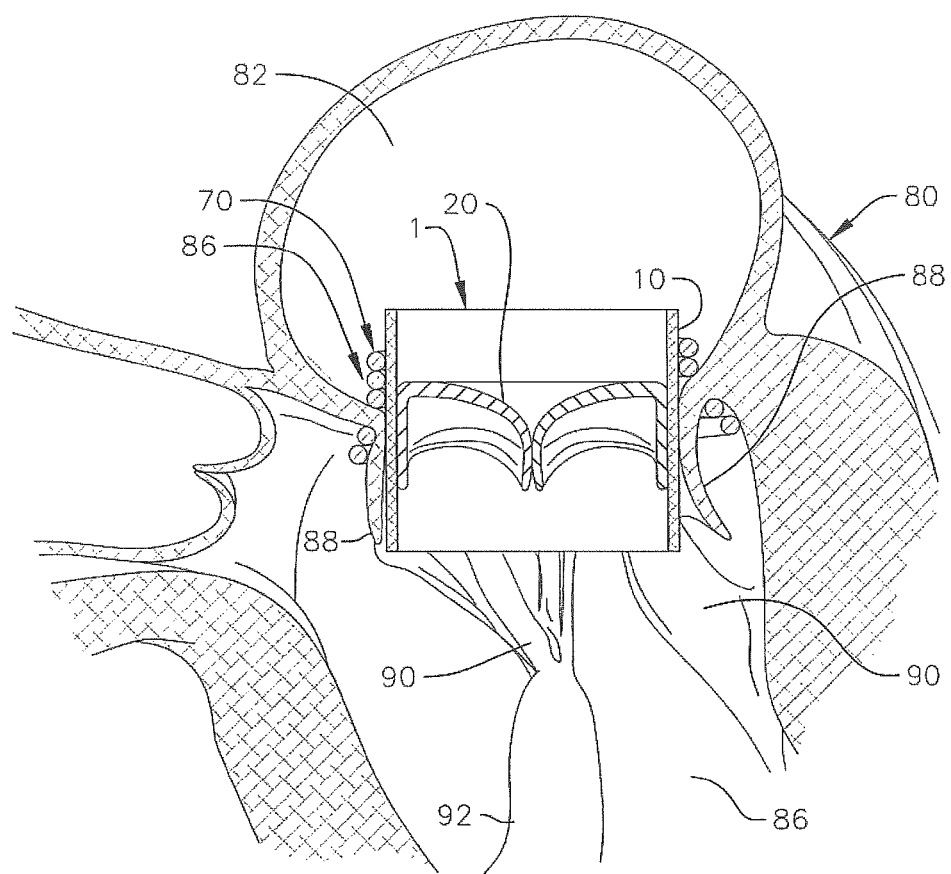
FIG. 4B illustrates a cross-sectional side view of a coil anchor deployed in the mitral position of the heart, with an implanted valve prosthesis, according to another embodiment.

FIGS. 4A and 4B show side cross-sectional views of embodiments of different anchors that can be used to facilitate implantation of the valve 1 at the mitral position of a patient's heart. As shown in FIGS. 4A and 4B, a left side of a heart 80 includes a left atrium 82, a left ventricle 84, and a mitral valve 86 connecting the left atrium 82 and the left ventricle 84. The mitral valve 86 includes anterior and posterior leaflets 88 that are connected to an inner wall of the left ventricle 84 via chordae tendineae 90 and papillary muscles 92.

In FIG. 4A, a first anchoring device includes a flexible ring or halo 60 that surrounds the native leaflets 88 of the mitral valve 86 and/or the chordae tendineae 90. The ring 60 pinches or urges portions of the leaflets inwards, in order to form a more circular opening at the mitral position, for more effective implantation of the prosthetic valve 1. The valve prosthesis 1 is retained in the native mitral valve annulus 86 by the ring anchor 60, and can be delivered to the position shown, for example, by positioning the valve 1 in the mitral annulus 86 while the valve 1 is crimped, and then expanding the valve 1 once it is positioned as shown in FIG. 4A. Once expanded, the valve 1 pushes outwardly against the ring anchor 60 to secure the positions of both the valve 1 and the ring anchor 60. In some embodiments, an undersized ring anchor 60 with an inner diameter that is slightly smaller than the diameter of the prosthetic valve 1 in its expanded state can be used, to provide stronger friction between the parts, leading to more secure attachment. As can be seen in FIG. 4A, at least a portion of the native mitral valve leaflets 88 and/or a portion of the chordae tendineae 90 are pinched or sandwiched between the valve 1 and the ring anchor 60 to secure the components to the native anatomy.

FIG. 4B is similar to FIG. 4A, except instead of a ring anchor 60, a helical anchor 70 is utilized instead. The helical anchor 70 can include more coils or turns than the ring anchor 60, and can extend both upstream and downstream of the mitral valve annulus 86. The helical anchor 70 in some situations can provide a greater and more secure attachment area against which the valve 1 can abut. Similar to the ring anchor 60 in FIG. 4A, at least a portion of the native mitral valve leaflets 88 and/or the chordae 90 are pinched between the valve 1 and the helical anchor 70. Methods and devices for implanting helical anchors and prosthetic valves are described in U.S. application Ser. No. 15/682,287, filed on Aug. 21, 2017, and U.S. application Ser. No. 15/684,836, filed on Aug. 23, 2017, which are incorporated herein by reference.

FIG. 4C illustrates another representative embodiment of a helical anchor 300 that can be used in combination with any of the prosthetic valves described herein. The anchor 300 can be configured as a coil having a central region 302, a lower region 304, and an upper region 306. The lower region 304 includes one or more turns in a helical arrangement that can be configured to encircle or capture the chordae tendineae and/or the leaflets of the mitral valve. The central region 302 includes a plurality of turns configured to retain the prosthetic valve in the native annulus. The upper region 306 includes one or more turns, and can be configured to keep the anchor from being dislodged from the valve annulus prior to implantation of the prosthetic valve. In some embodiments, the upper region 306 can be positioned over the floor of the left atrium, and can be configured to keep the turns of the central region 302 positioned high within the mitral apparatus.

The anchor 300 also includes an extension portion 308 positioned between the central region 302 and the upper region 306. In other embodiments, the extension portion 308 can instead be positioned, for example, wholly in the central region 302 (e.g., at an upper portion of the central region) or wholly in the upper region 306. The extension portion 308 includes a part of the coil that extends substantially parallel to a central axis of the anchor. In other embodiments, the extension portion 308 can be angled relative to the central axis of the anchor. The extension portion 308 can serve to space the central region 302 and the upper region 306 apart from one another in a direction along the central axis so that a gap is formed between the atrial side and the ventricular side of the anchor.

The extension portion 308 of the anchor is intended to be positioned through or near the native valve annulus, in order to reduce the amount of the anchor that passes through, pushes, or rests against the native annulus and/or the native leaflets when the anchor is implanted. This can reduce the force applied by the anchor on the native mitral valve and reduce abrasion of the native leaflets. In one arrangement, the extension portion 308 is positioned at and passes through one of the commissures of the native mitral valve. In this manner, the extension portion 308 can space the upper region 306 apart from the native leaflets of the mitral valve to prevent the upper region 306 from interacting with the native leaflets from the atrial side. The extension portion 308 also elevates the upper region 306 such that the upper region contacts the atrial wall above the native valve, which can reduce the stress on and around the native valve, as well as provide for better retention of the anchor.

In the illustrated embodiment, the anchor 300 can further include one or more openings configured as through holes 310 at or near one or both of the proximal and distal ends of the anchor. The through holes 310 can serve, for example, as suturing holes for attaching a cover layer over the coil of the anchor, or as an attachment site for delivery tools such as a pull wire for a pusher or other advancement device. In some embodiments, a width or thickness of the coil of the anchor 300 can also be varied along the length of the anchor. For example, a central portion of the anchor can be made thinner than end portions of the anchor. This can allow the central portion to exhibit greater flexibility, while the end portions can be stronger or more robust. In certain examples, making the end portions of the coil relatively thicker can also provide more surface area for suturing or otherwise attaching a cover layer to the coil of the anchor.

In certain embodiments, the helical anchor 300 can be configured for insertion through the native valve annulus in a counter-clockwise direction. For example, the anchor can be advanced through commissure A3P3, commissure A1P1, or through another part of the native mitral valve. The counter-clockwise direction of the coil of the anchor 300 can also allow for bending of the distal end of the delivery catheter in a similar counter-clockwise direction, which can be easier to achieve than to bend the delivery catheter in the clockwise direction. However, it should be understood that the anchor can be configured for either clockwise or counter-clockwise insertion through the valve, as desired.

Returning to the prosthetic valve of FIG. 3, the prosthetic valve 1 generally includes a metal frame 10 that forms a number of edges. In addition, many frames 10 are constructed with edged crowns or apices 14 and protruding commissure attachment posts 11, as well as threads 40 that can be exposed along an outer surface of the frame 10. These features can cause damage to the native mitral tissue, such as tissue lodged between the prosthetic valve 1 and the anchor 60, 70, for example, by movement or friction between the native tissue and the various abrasive surfaces of the prosthetic valve 1. In addition, other native tissue in close proximity to the prosthetic valve 1, such as the chordae tendinae, can also potentially be damaged.

Figure 5:
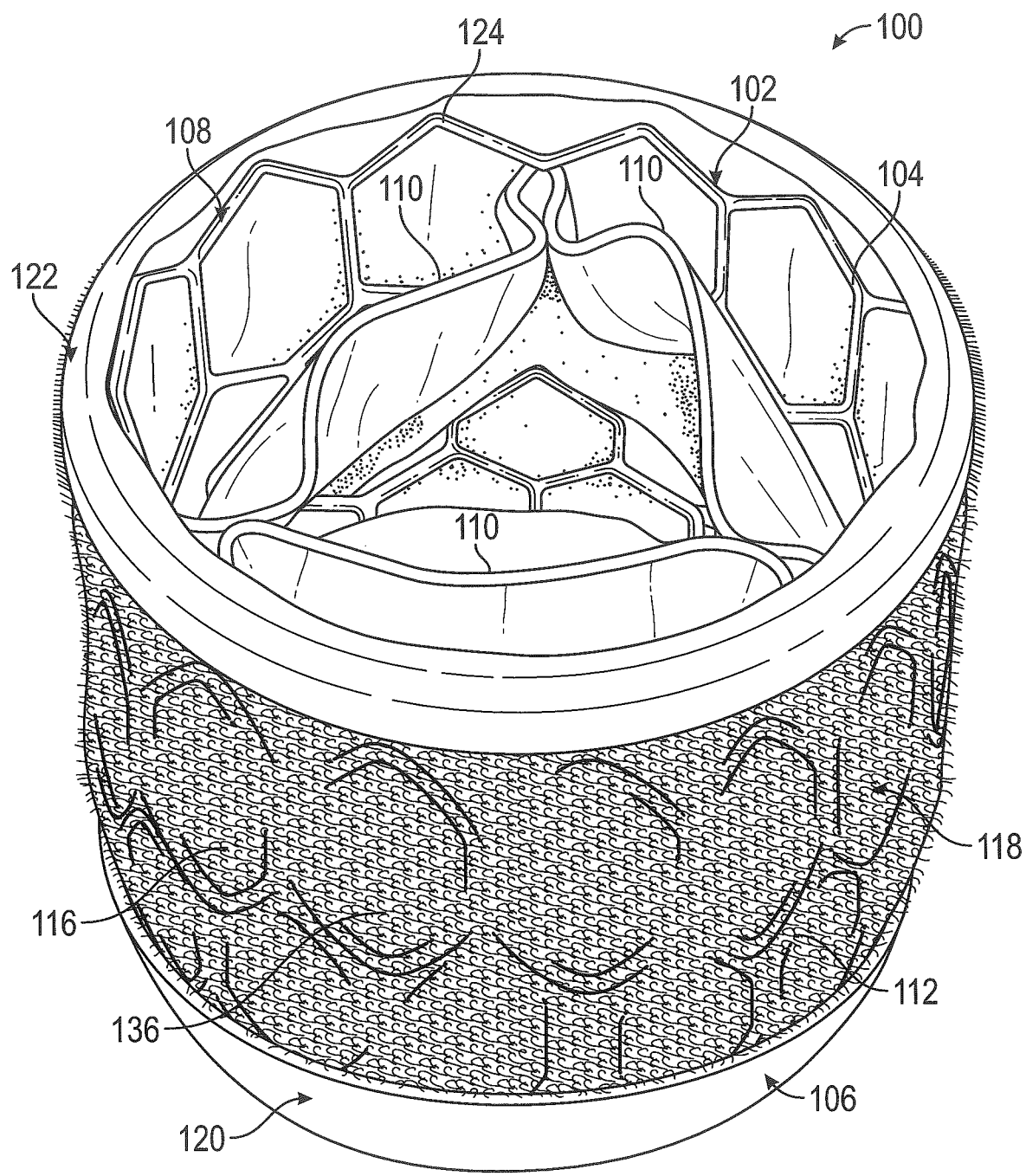
FIG. 5 is a perspective view of a prosthetic heart valve including a representative embodiment of a covering.
Figure 6:
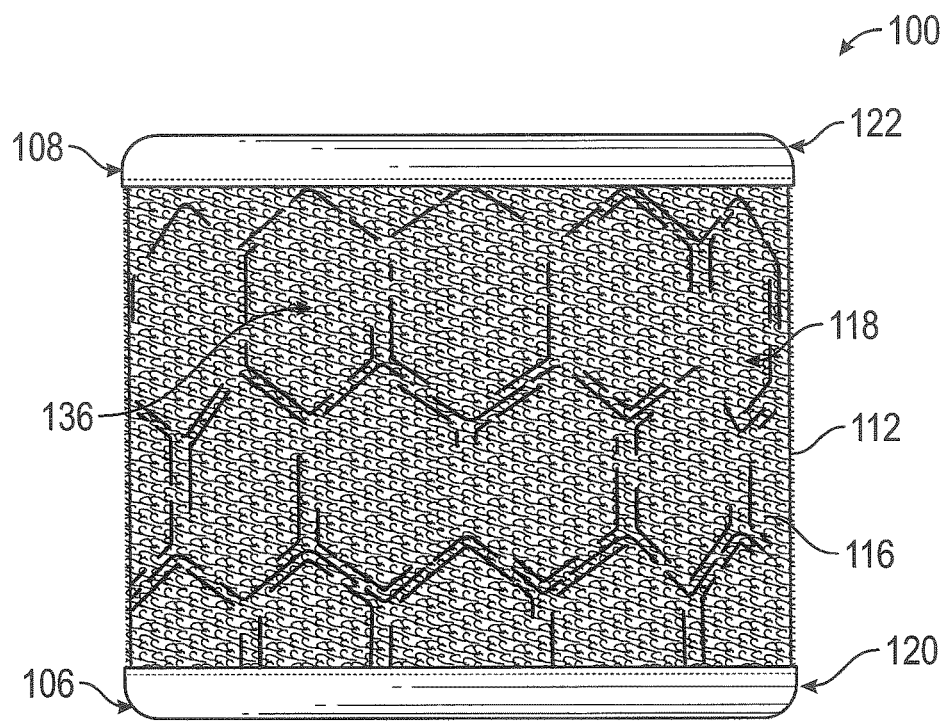
FIG. 6 is a side-elevation view of the prosthetic heart valve of FIG. 5.
Figure 7:
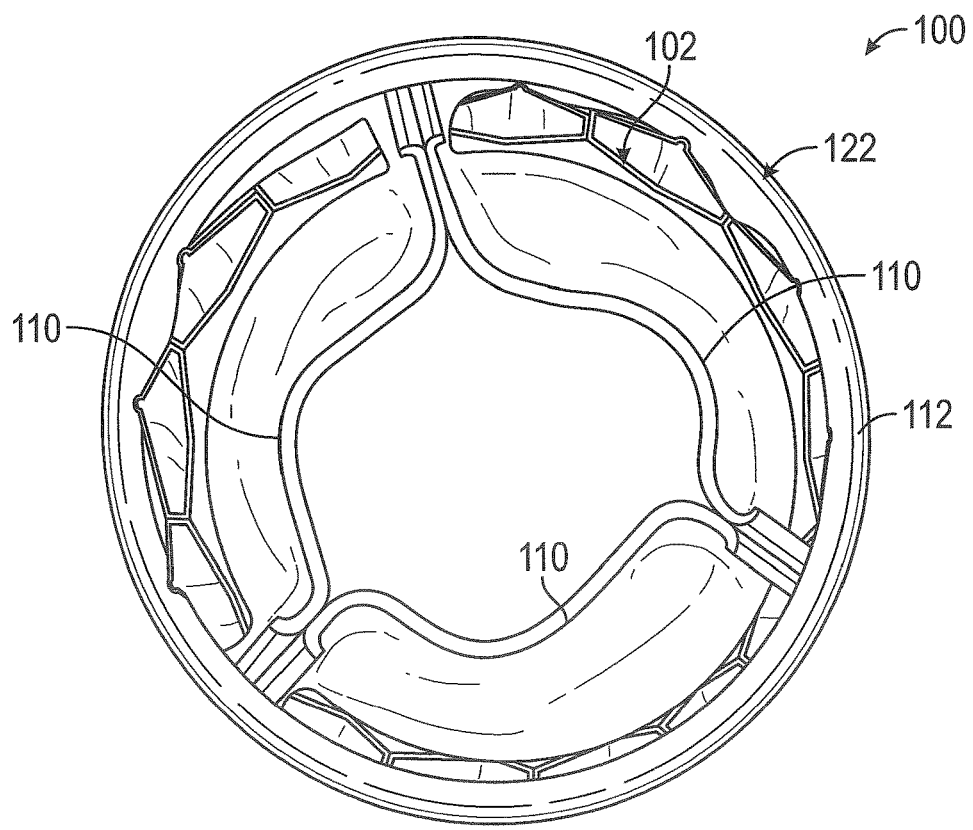
FIG. 7 is a top plan view of the prosthetic heart valve of FIG. 5.

FIGS. 5-7 illustrate a representative embodiment of a prosthetic heart valve 100 similar to the Edwards Lifesciences SAPIEN™ 3 valve, which is described in detail in U.S. Pat. No. 9,393,110, which is incorporated herein by reference. The prosthetic valve 100 includes a frame 102 formed by a plurality of angled strut members 104, and having an inflow end 106 and an outflow end 108. The prosthetic valve 100 also includes a leaflet structure comprising three leaflets 110 situated at least partially within the frame 102 and configured to collapse in a tricuspid arrangement similar to the aortic valve, although the prosthetic valve can also include two leaflets configured to collapse in a bicuspid arrangement in the manner of the mitral valve, or more than three leaflets, as desired. The strut members 104 can form a plurality of apices 124 arranged around the inflow and outflow ends of the frame.

The prosthetic heart valve can include an outer covering 112 configured to cushion (protect) native tissue in contact with the prosthetic valve after implantation, and to reduce damage to the tissue due to movement or friction between the tissue and surfaces of the valve. The covering 112 can also reduce paravalvular leakage. In the embodiment of FIG. 5, the covering 112 includes a first layer configured as a backing layer 114 (see, e.g., FIG. 8), and a second layer configured as a cushioning layer 116. The cushioning layer 116 can be disposed on the backing layer 114, and can comprise a soft, plush surface 118 oriented radially outward so as to protect tissue or objects in contact with the cushioning layer. In the illustrated configuration, the covering 112 also includes an atraumatic inflow protective portion 120 extending circumferentially around the inflow end 106 of the frame, and an atraumatic outflow protective portion 122 extending circumferentially around the outflow end 108 of the frame. The portion of the cushioning layer 116 between the inflow and outflow protective portions 120, 122 can define a main cushioning portion 136.

Figure 8:
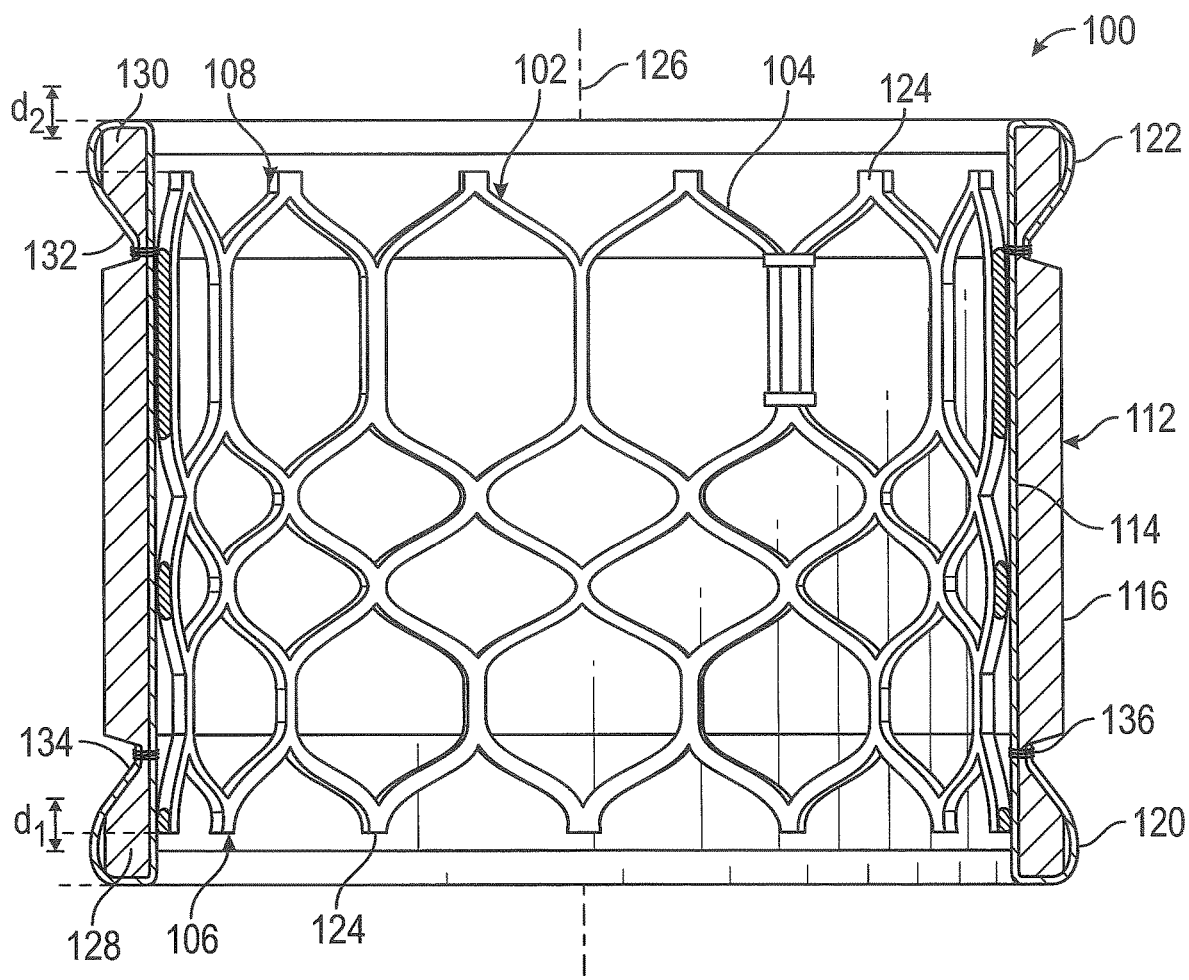
FIG. 8 is a cross-sectional side elevation view of the prosthetic heart valve of FIG. 5.

FIG. 8 is a cross-sectional view schematically illustrating the prosthetic valve 100 with the leaflet structure removed for purposes of illustration. The covering 112 extends around the exterior of the frame 102, such that an interior surface of the backing layer 114 is adjacent or against the exterior surfaces of the strut members 104. As illustrated in FIG. 8, the cushioning layer 116 can have a length that is greater than the length of the frame as measured along a longitudinal axis 126 of the frame. Thus, the covering 112 can be situated such that the cushioning layer 116 extends distally (e.g., in the upstream direction) beyond the apices 124 of the strut members at the inflow end 106 of the frame, with the portion of the cushioning layer extending beyond the apices being referred to herein as distal end portion 128. At the opposite end of the valve, the cushioning layer 116 can extend proximally (e.g., in the downstream direction) beyond the apices 124 of the strut members, with the portion located beyond the apices being referred to as proximal end portion 130. The distances by which the proximal and distal end portions 128, 130 of the cushioning layer 116 extend beyond the apices at the respective end of the valve can be the same or different depending upon, for example, the dimensions of the valve, the particular application, etc.

The backing layer 114 can have sufficient length in the axial direction such that a proximal end portion or flap 132 of the backing layer 114 can be folded over the proximal end portion 130 of the cushioning layer 116 in the manner of a cuff to form the outflow protective portion 122. Meanwhile, a distal end portion or flap 134 of the backing layer 114 can be folded over the distal end portion 128 of the cushioning layer 116 to form the inflow protective portion 120. The proximal and distal flaps 132, 134 of the backing layer 116 can be secured to the underlying section of the backing layer by, for example, sutures 136. In this manner, the inflow and outflow protective portions 120, 122 are constructed such that the proximal and distal end portions 130, 128 of the cushioning layer 116 are at least partially enclosed by the flaps 132, 134 of the backing layer 116. This construction provides sufficient strength and resistance to bending to the inflow and outflow protective portions 120, 122 so that they extend along the longitudinal axis 126 of the valve without bending or otherwise protruding into the inner diameter of the valve (e.g., by bending under their own weight, by blood flow, or by blood pressure). In this manner, the inflow and outflow protective portions 120, 122 minimally impact flow through the prosthetic valve and avoid interfering with the prosthetic valve leaflets, reducing flow disturbances and the risk of thrombus.

In the illustrated configuration, the inflow protective portion 120 can extend beyond the apices 124 of the strut members at the inflow end of the frame by a distance $d_1$, and the outflow protective portion 122 can extend beyond the apices 124 of the strut members at the outflow end of the frame by a distance $d_2$. The distances $d_1$ and $d_2$ can be the same or different, depending upon the type of prosthetic valve, the treatment location, etc. For example, for a 29 mm prosthetic valve, the distances $d_1$ and $d_2$ can be from about 0.5 mm to about 3 mm. In a representative embodiment, the distances $d_1$ and $d_2$ can be from about 1 mm to about 2 mm. Because the inflow and outflow protective portions 120, 122 extend beyond the apices 124 of the respective ends of the frame, the inflow and outflow protective portions can shield adjacent tissue and/or another implant adjacent the prosthetic valve from contacting the apices 124 of the frame.

Figure 10:
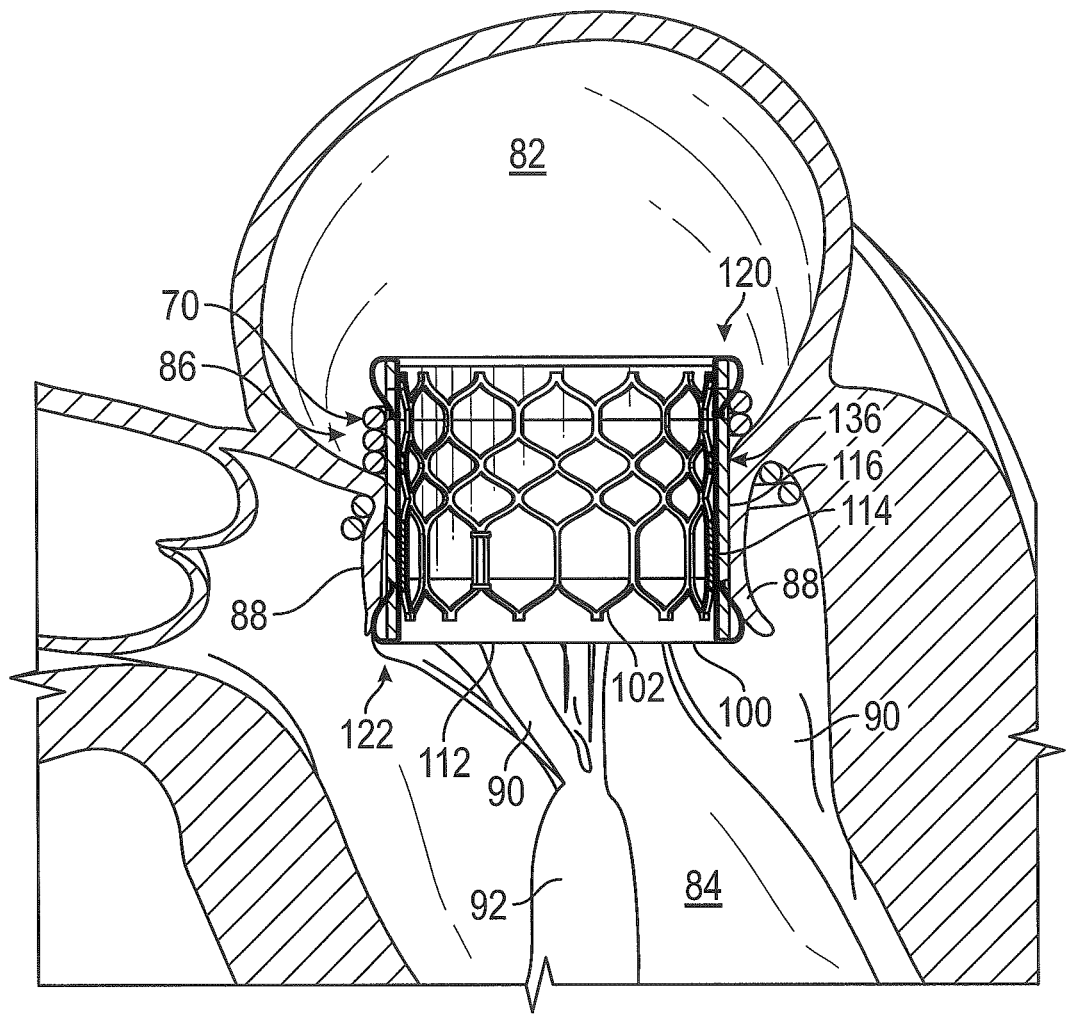
FIG. 10 is a cross-sectional side view of the prosthetic heart valve of FIG. 5 deployed in the mitral position of the heart.

For example, FIG. 10 illustrates the prosthetic valve 100 implanted within a helical anchor 70 in the native mitral valve 86, similar to FIGS. 4A and 4B above. In the illustrated example, the inflow end portion of the prosthetic valve is positioned above the superior surface of the native mitral valve annulus and spaced from surrounding tissue. However, in other implementations, depending on the axial positioning of the prosthetic valve, the inflow protective portion 120 can contact the native leaflets 88 and prevent them from directly contacting the apices 124 at the inflow end of the frame. Depending on the diameter of the prosthetic valve at the inflow end, the inflow protective portion 120 can serve to prevent the atrium wall from directly contacting the apices 124 at the inflow end of the frame.

As shown in FIG. 10, the anchor 70 can also rest against the compliant inflow protective portion 120. Meanwhile, the portions of the native leaflets 88 captured between the anchor 70 and the prosthetic valve 100 can be cushioned by the plush surface 118 of the main cushioning portion 136. In certain embodiments, the soft, compliant nature and texture of the cushioning layer 116 can increase friction between the native leaflets and the prosthetic valve. This can reduce relative movement of the native leaflets and the prosthetic valve as the left ventricle expands and contracts, reducing the likelihood of damage to the native leaflets and the surrounding tissue. The cushioning layer 116 can also provide increased retention forces between the anchor 70 and the prosthetic valve 100. The plush, compressible nature of the cushioning layer 116 can also reduce penetration of the covering 112 through the openings in the frame 102 caused by application of pressure to the covering, thereby reducing interference with the hemodynamics of the valve. Additionally, the outflow cushioning portion 122 can protect the chordae tendineae 90 from contacting the strut members of the frame, and in particular the apices 124 at the outflow end of the frame, thereby reducing the risk of injury or rupture of the chordae.

The backing layer 114 can comprise, for example, any of various woven fabrics, such as gauze, polyethylene terephthalate (PET) fabric (e.g., Dacron), polyester fabric, polyamide fabric, or any of various non-woven fabrics, such as felt. In certain embodiments, the backing layer 114 can also comprise a film including any of a variety of crystalline or semi-crystalline polymeric materials, such as polytetrafluoroethylene (PTFE), PET, polypropylene, polyamide, polyetheretherketone (PEEK), etc. In this manner, the backing layer 114 can be relatively thin and yet strong enough to allow the covering 112 to be sutured to the frame, and to allow the prosthetic valve to be crimped, without tearing.

Figure 9:
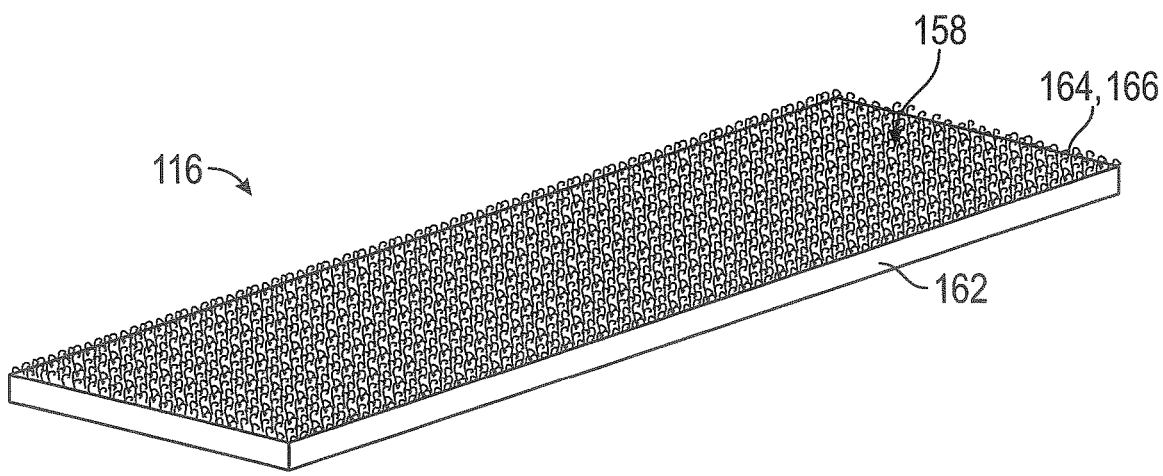
FIG. 9 is a perspective view of a representative embodiment of a cushioning layer including a plush pile.

As stated above, the cushioning layer 116 can comprise at least one soft, plush surface 118. In certain examples, the cushioning layer 116 can be made from any of a variety of woven or knitted fabrics wherein the surface 116 is the surface of a plush nap or pile of the fabric. Exemplary fabrics having a pile include velour, velvet, velveteen, corduroy, terrycloth, fleece, etc. FIG. 9 illustrates a representative embodiment of the cushioning layer 116 in greater detail. In the embodiment of FIG. 9, the cushioning layer 116 can have a base layer 162 (a first layer) from which the pile 158 (a second layer) extends. The base layer 162 can comprise warp and weft yarns woven or knitted into a mesh-like structure. For example, in a representative configuration, the yarns of the base layer 162 can be flat yarns with a denier range of from about 7 dtex to about 100 dtex, and can be knitted with a density of from about 20 to about 100 wales per inch and from about 30 to about 110 courses per inch. The yarns can be made from, for example, biocompatible thermoplastic polymers such as PET, Nylon, ePTFE, etc., other suitable natural or synthetic fibers, or soft monolithic materials.

Figure 11:
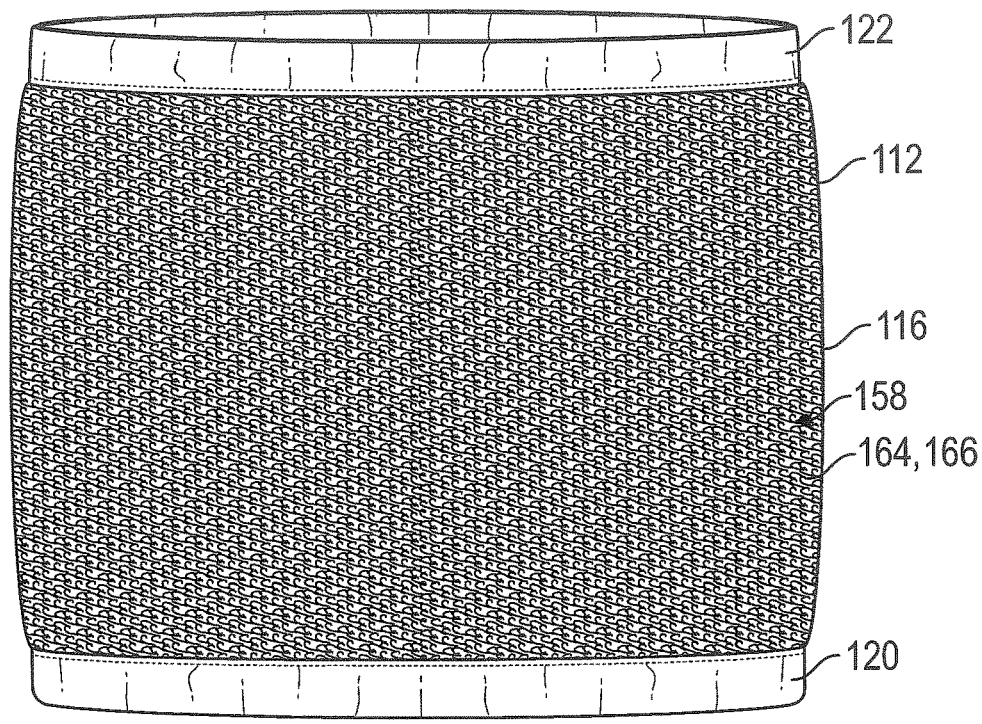
FIG. 11 is a side elevation view of a prosthetic heart valve including another embodiment of a covering.

The pile 158 can comprise pile yarns 164 woven or knitted into loops. In certain configurations, the pile yarns 164 can be the warp yarns or the weft yarns of the base layer 162 woven or knitted to form the loops. The pile yarns 164 can also be separate yarns incorporated into the base layer, depending upon the particular characteristics desired. In certain embodiments, the loops can be cut such that the pile 158 is a cut pile in the manner of, for example, a velour fabric. FIGS. 5-8 illustrate a representative embodiment of the cushioning layer 116 configured as a velour fabric. In other embodiments, the loops can be left intact to form a looped pile in the manner of, for example, terrycloth. FIG. 9 illustrates a representative embodiment of the cushioning layer 116 in which the pile yarns 164 are knitted to form loops 166. FIG. 11 illustrates an embodiment of the covering 112 incorporating the cushioning layer 116 of FIG. 9.

In some configurations, the pile yarns 164 can be textured yarns having an increased surface area due to, for example, a wavy or undulating structure. In configurations such as the looped pile embodiment of FIG. 11, the loop structure and the increased surface area provided by the textured yarn of the loops 166 can allow the loops to act as a scaffold for tissue growth into and around the loops of the pile. Promoting tissue growth into the pile 158 can increase retention of the valve at the implant site and contribute to long-term stability of the valve.

The cushioning layer embodiments described herein can also contribute to improved compressibility and shape memory properties of the covering 112 over known valve coverings and skirts. For example, the pile 158 can be compliant such that it compresses under load (e.g., when in contact with tissue, implants, or the like), and returns to its original size and shape when the load is relieved. This can help to improve sealing between the cushioning layer 116 and, for example, support structures or other devices such as the helical anchor 70 in which the prosthetic valve is deployed, or between the cushioning layer and the walls of the native annulus. The compressibility provided by the pile 158 of the cushioning layer 116 is also beneficial in reducing the crimp profile of the prosthetic valve. Additionally, the covering 112 can prevent the leaflets 110 or portions thereof from extending through spaces between the strut members 104 as the prosthetic valve is crimped, thereby reducing damage to the prosthetic leaflets due to pinching of the leaflets between struts.

In alternative embodiments, the cushioning layer 116 be made of non-woven fabric such as felt, or fibers such as non-woven cotton fibers. The cushioning layer 116 can also be made of porous or spongey materials such as, for example, any of a variety of compliant polymeric foam materials, or woven or knitted fabrics, such as woven or knitted PET. In further alternative embodiments, the proximal and distal end portions of the cushioning layer 116 of the embodiment of FIG. 11 can be free of loops 166, and the inflow and outflow protective portions 120, 122 can be formed by folding the base layer 162 back on itself to form cuffs at the inflow and outflow ends of the valve.

Figure 12:
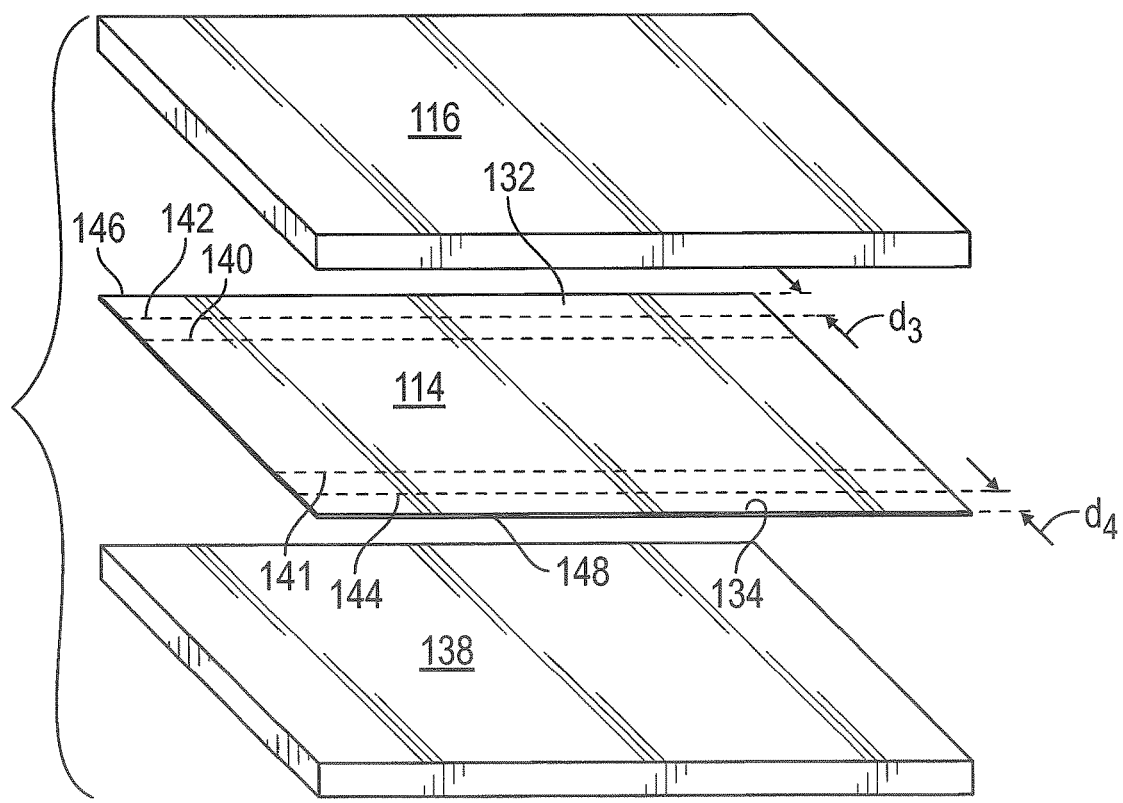
FIG. 12 is a perspective view of a backing layer, a stencil for producing the backing layer, and a cushioning layer, before the backing layer and the cushioning layer are secured together.
Figure 18:
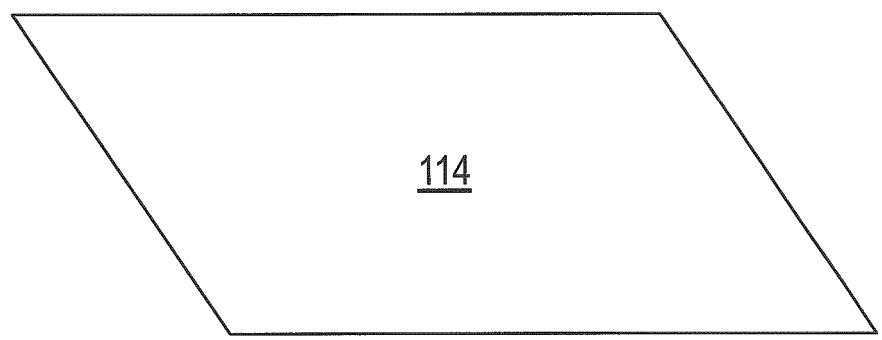
FIG. 18 is a top plan view of an embodiment of a backing layer after it is cut using a parallelogram stencil.

In a representative example illustrated in FIG. 12, the covering 112 of FIGS. 5-8 can be made by cutting a fabric material (e.g., a PET fabric) with a stencil 138 to form the backing layer 114. In the illustrated embodiment, the stencil 138 is shaped like a parallelogram, although other configurations are possible. The angles of the corners of the stencil 138 can be shaped such that the fabric material is cut at about a 45 degree angle relative to the direction of the fibers of the fabric. This can improve the crimpability of the resulting backing layer 114 by, for example, allowing the backing layer to stretch along a direction diagonal to the warp and weft yarns. FIG. 18 illustrates a plan view of a representative example of the backing layer 114 after being cut using the parallelogram stencil 138.

The cushioning layer 116 can be attached (e.g., by sutures, adhesive, etc.) to the backing layer 114. In FIG. 12, the location of the proximal and distal ends of the frame 102 when the covering is attached to the frame are represented as dashed lines 140, 141 on the backing layer 114. Meanwhile, dashed lines 142, 144 represent the location of the proximal and distal edges of the cushioning layer 116 once the cushioning layer is secured to the backing layer. For example, the cushioning layer 116 can be sutured to the backing layer 114 along the proximal and distal edges at or near lines 142, 144. As shown in FIG. 12, line 142 representing the proximal edge of the cushioning layer 116 can be offset from the proximal edge 146 of the backing layer 114 by a distance $d_3$ to create the proximal flap 132. Meanwhile, line 144 representing the distal edge of the cushioning layer 116 can be offset from the distal edge 148 of the backing layer 114 by a distance $d_4$ to create the distal flap 134. The distances $d_3$ and $d_4$ can be the same or different, as desired. For example, depending upon the size of the valve and the size of the inflow and outflow cushioning portions, the distances $d_3$ and $d_4$ can be, for example, about 3-5 mm. In some embodiments, the distances $d_3$ and $d_4$ can be about 3.5 mm.

Once the cushioning layer 116 is secured to the backing layer 114, the resulting swatch can be folded and sutured into a cylindrical shape. The flaps 132, 134 of the backing layer 114 can be folded over the edges of the cushioning layer 116 and sutured to form the inflow and outflow protective portions 120, 122. The resulting covering 112 can then be secured to the frame 102 by, for example, suturing it the strut members 104.

Figure 13:
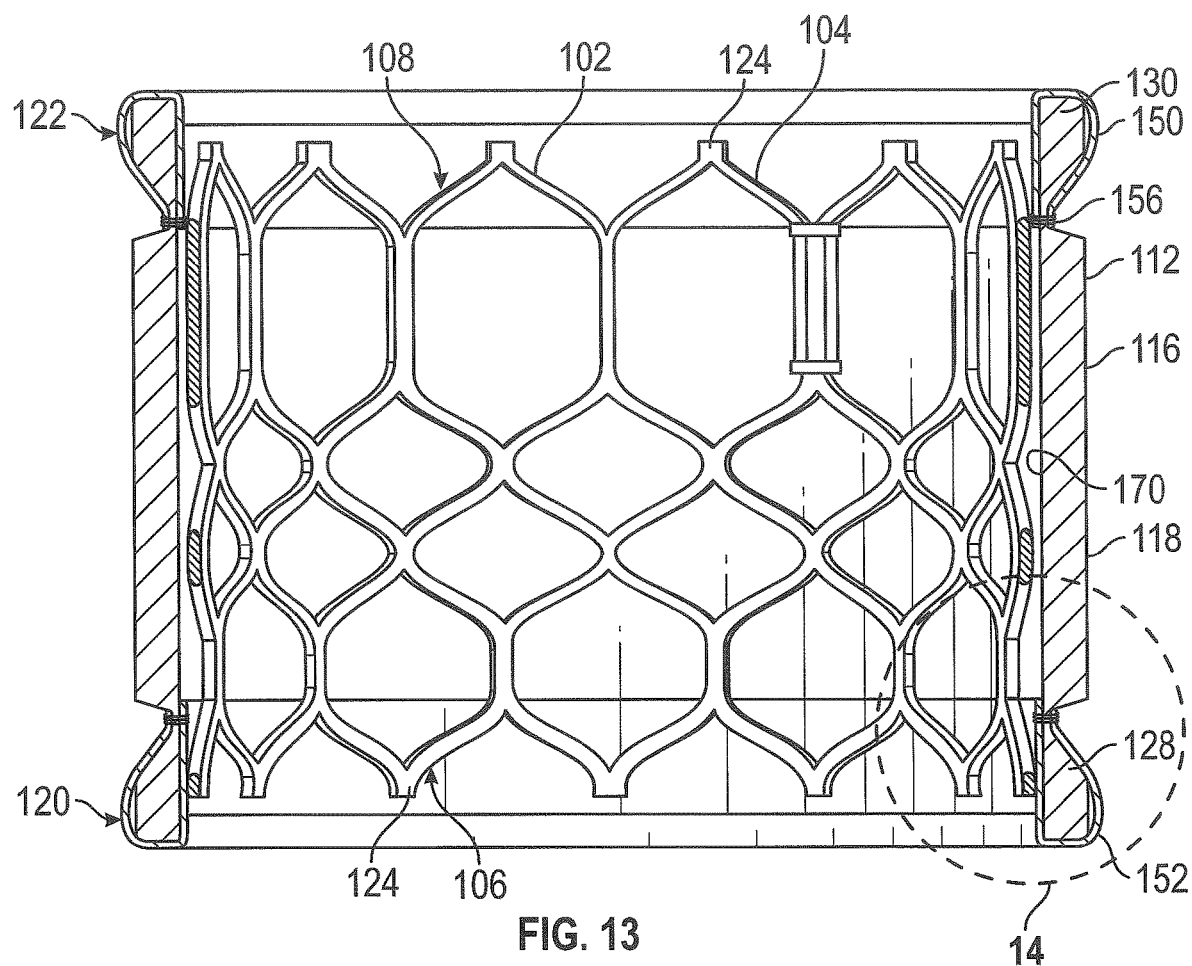
FIG. 13 is a cross-sectional side elevation view of a prosthetic heart valve including another embodiment of a covering.
Figure 14:
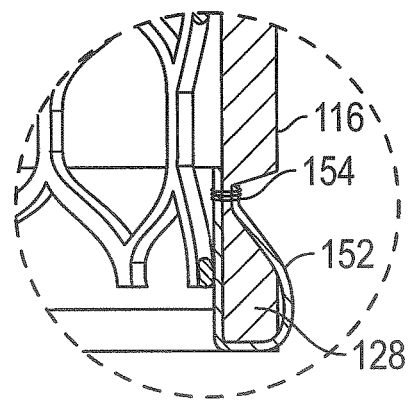
FIG. 14 is a detail view of an inflow protective portion of the covering of FIG. 13.

FIGS. 13 and 14 illustrate another embodiment of the covering 112 in which the inflow and outflow protective portions 120, 122 are formed with separate pieces of material that wrap around the ends of the cushioning layer 116 at the inflow and outflow ends of the valve. For example, the proximal end portion 130 of the cushioning layer 116 can be covered by a member configured as a strip 150 of material that wraps around the cushioning layer from the interior surface 170 (e.g., the surface adjacent the frame) of the cushioning layer 116, over the circumferential edge of the proximal end portion 130, and onto the exterior surface 118 of the cushioning layer to form the outflow protective portion 122. Likewise, a material strip member 152 can extend from the interior surface 170 of the cushioning layer, over the circumferential edge of the distal end portion 128, and onto the exterior surface of the cushioning layer to form the inflow protective portion 120. The strip members 150, 152 can be sutured to the cushioning layer 116 along the proximal and distal edge portions 130, 128 of the cushioning layer at suture lines 154, 156, respectively.

In certain configurations, the strip members 150, 152 can be made from any of various natural materials and/or tissues, such as pericardial tissue (e.g., bovine pericardial tissue). The strip members 150, 152 can also be made of any of various synthetic materials, such as PET and/or expanded polytetrafluoroethylene (ePTFE). In some configurations, making the strip members 150, 152 from natural tissues such as pericardial tissue can provide desirable properties such as strength, durability, fatigue resistance, and compliance, and cushioning and reduced friction with materials or tissues surrounding the implant.

Figure 15:
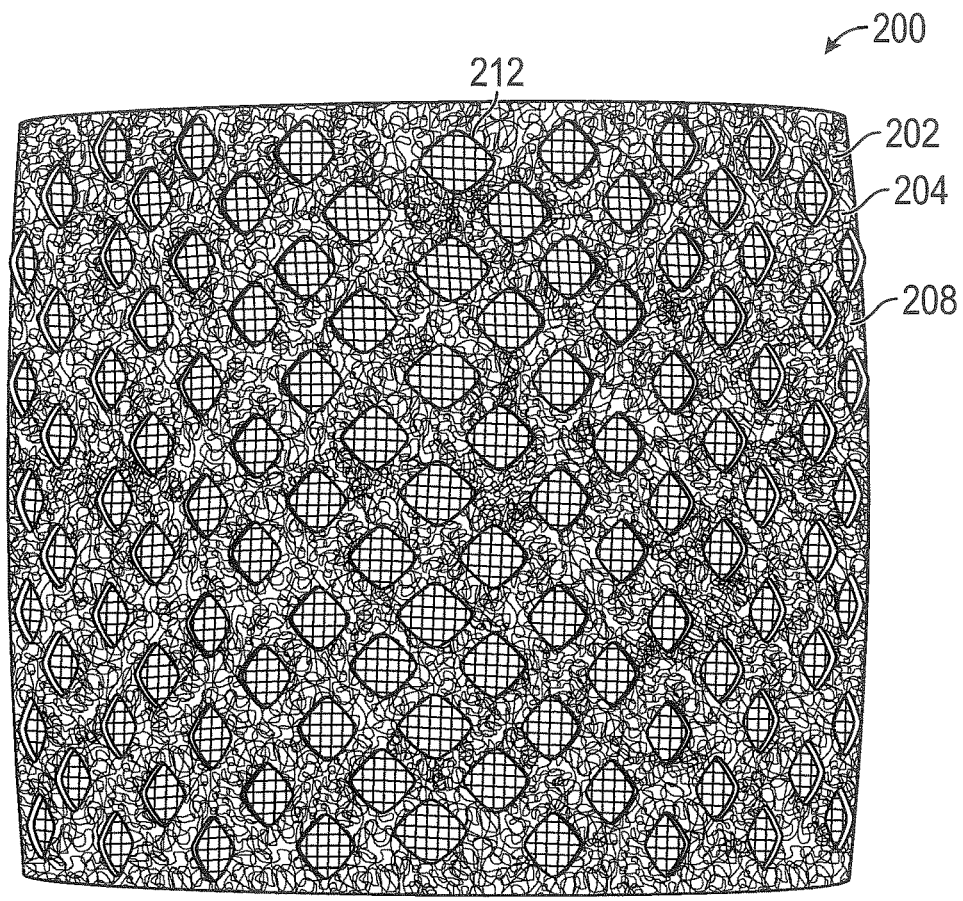
FIG. 15 is a side elevation view of a prosthetic heart valve including another embodiment of a covering comprising a spacer fabric.

FIG. 15 illustrates a prosthetic valve 200 including another embodiment of an outer covering 202 comprising a cushioning layer 204 made of a spacer fabric. In the illustrated embodiment, the outer covering 202 is shown without inflow and outflow protective portions, and with the cushioning layer 204 extending along the full length of the frame from the inflow end to the outflow end of the valve. However, the outer covering 202 may also include inflow and/or outflow protective portions, as described elsewhere herein.

Figure 16:
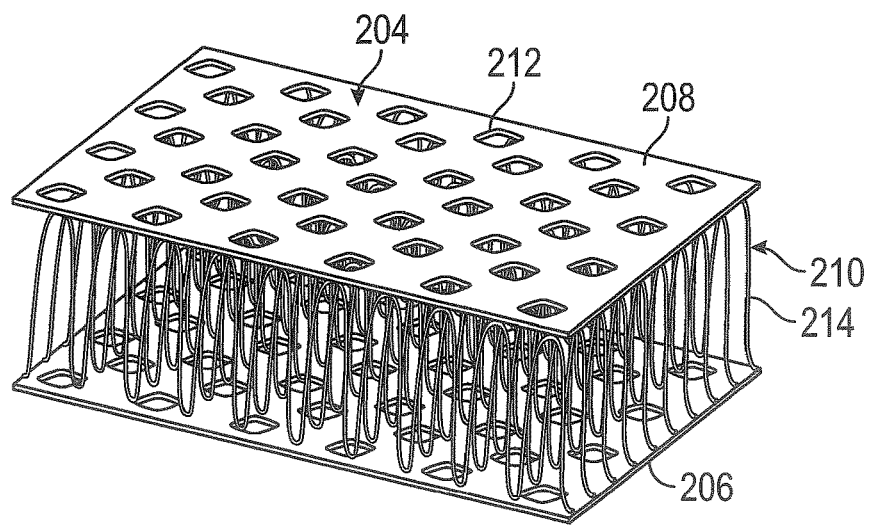
FIG. 16 is a perspective view of a representative embodiment of a spacer cloth including looped pile yarns.
Figure 17:
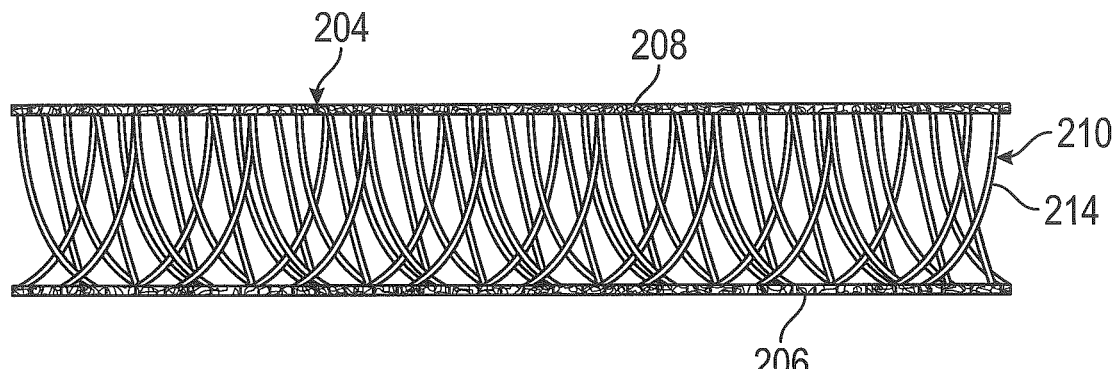
FIG. 17 is a side elevation view of the spacer fabric of FIG. 16.

Referring to FIGS. 16 and 17, the spacer fabric cushioning layer can comprise a first layer 206, a second layer 208, and a spacer layer 210 extending between the first and second layers to create a three-dimensional fabric. The first and second layers 206, 208 can be woven fabric or mesh layers. In certain configurations, one or more of the first and second layers 206, 208 can be woven such that they define a plurality of openings 212. In some examples, openings such as the openings 212 can promote tissue growth into the covering 202. In other embodiments, the layers 206, 208 need not define openings, but can be porous, as desired.

The spacer layer 210 can comprise a plurality of pile yarns 214. The pile yarns 214 can be, for example, monofilament yarns arranged to form a scaffold-like structure between the first and second layers 206, 208. For example, FIGS. 16 and 17 illustrate an embodiment in which the pile yarns 214 extend between the first and second layers 206, 208 in a sinusoidal or looping pattern.

In certain examples, the pile yarns 214 can have a rigidity that is greater than the rigidity of the fabric of the first and second layers 206, 208 such that the pile yarns 214 can extend between the first and second layers 206, 208 without collapsing under the weight of the second layer 208. The pile yarns 214 can also be sufficiently resilient such that the pile yarns can bend or give when subjected to a load, allowing the fabric to compress, and return to their non-deflected state when the load is removed.

The spacer fabric can be warp-knitted, or weft-knitted, as desired. Some configurations of the spacer cloth can be made on a double-bar knitting machine. In a representative example, the yarns of the first and second layers 206, 208 can have a denier range of from about 10 dtex to about 70 dtex, and the yarns of the monofilament pile yarns 214 can have a denier range of from about 2 mil to about 10 mil. The pile yarns 214 can have a knitting density of from about 20 to about 100 wales per inch, and from about 30 to about 110 courses per inch. Additionally, in some configurations (e.g., warp-knitted spacer fabrics) materials with different flexibility properties may be incorporated into the spacer cloth to improve the overall flexibility of the spacer cloth.

Figure 19:
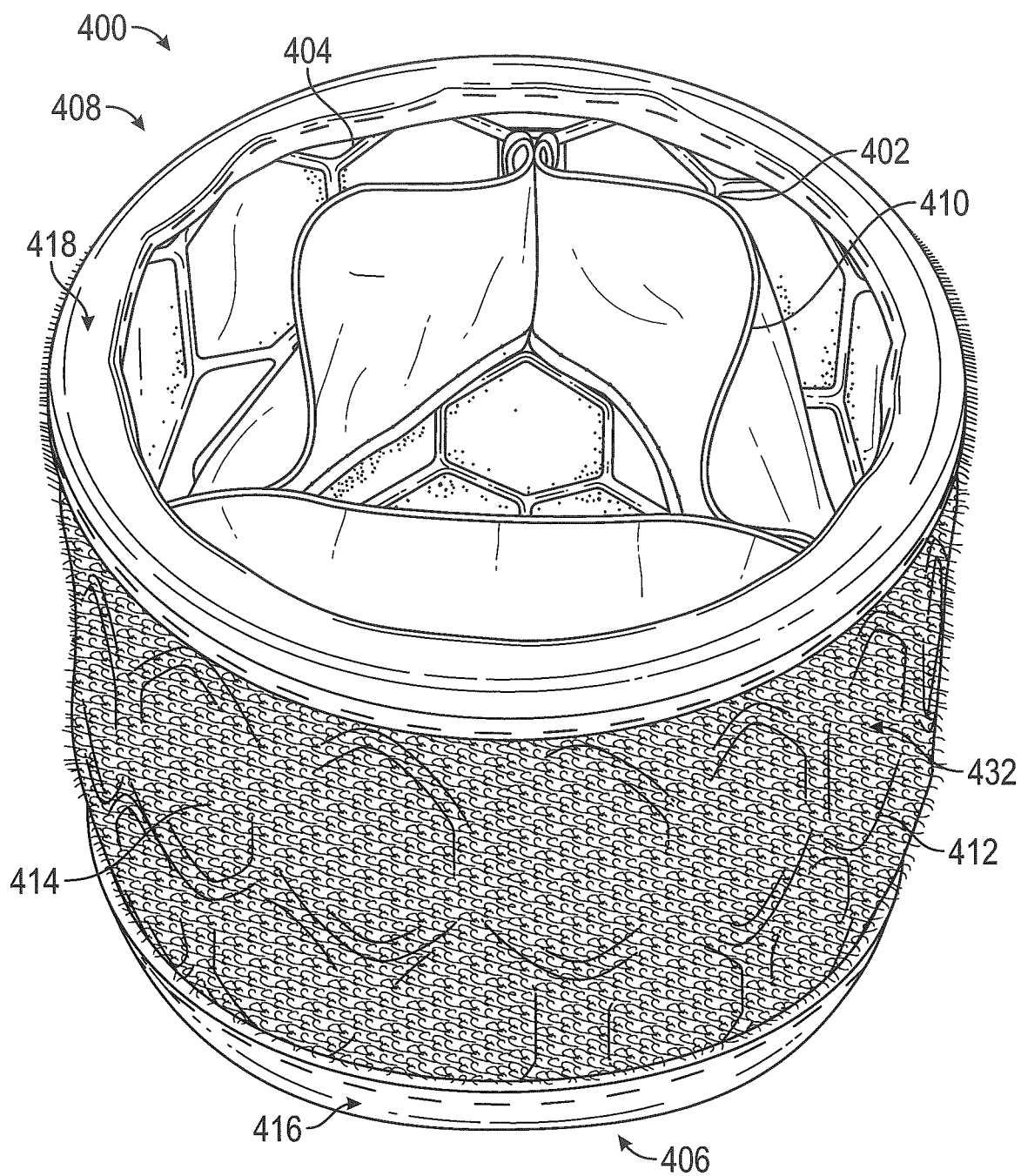
FIG. 19 is a perspective view of a prosthetic heart valve including another embodiment of a covering.
Figure 20:
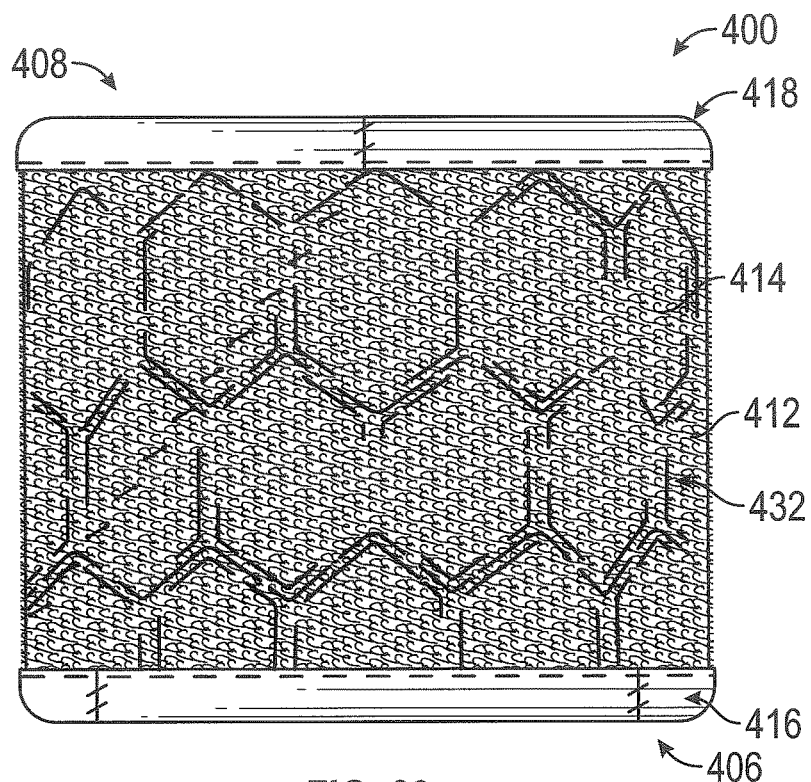
FIG. 20 is a side elevation view of the prosthetic heart valve of FIG. 19.
Figure 21:
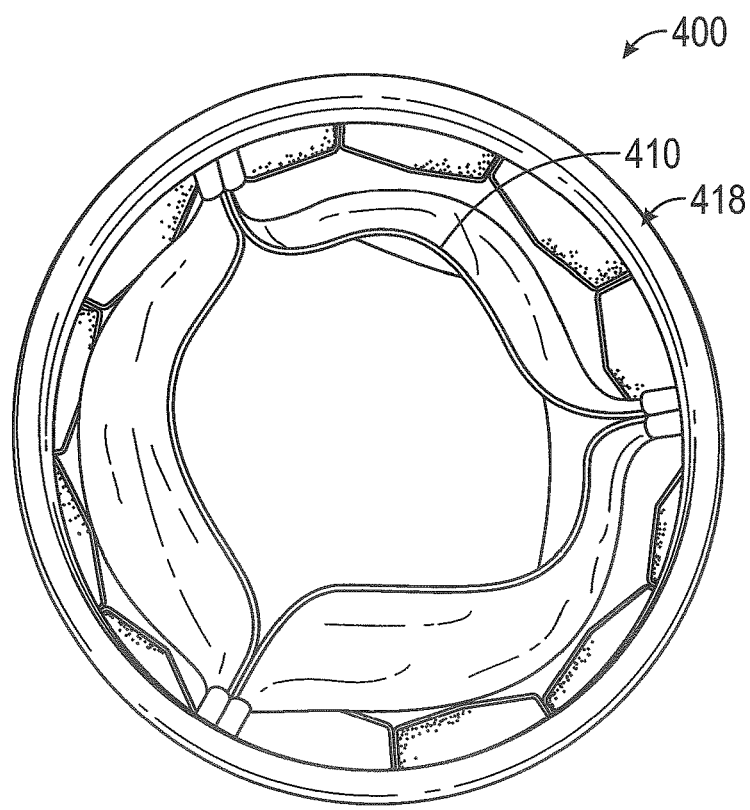
FIG. 21 is a plan view of an outflow end of the prosthetic heart valve of FIG. 19.

FIGS. 19-21 illustrate another embodiment of a prosthetic heart valve 400 including an outer covering with inflow and outflow protective portions that encapsulate the apices of the strut members. For example, the prosthetic valve can include a frame 402 formed by a plurality of strut members 404 defining apices 420 (FIGS. 22 and 24), and can have an inflow end 406 and an outflow end 408. A plurality of leaflets 410 can be situated at least partially within the frame 402.

The prosthetic valve can include an outer covering 412 situated about the frame 402. The outer covering 412 can include a main cushioning layer 414 including a plush exterior surface 432 (e.g., a first surface), similar to the cushioning layer 116 of FIG. 13 above. The covering 412 can also include an inflow protective portion 416 extending circumferentially around the inflow end 406 of the valve, and an outflow protective portion 418 extending circumferentially around the outflow end 408 of the valve. The inflow and outflow protective portions 416, 418 can be formed with separate pieces of material that are folded around the circumferential ends of the cushioning layer 414 at the inflow and outflow ends of the valve such that the protective portions encapsulate the apices 420 of the strut members.

Figure 22:
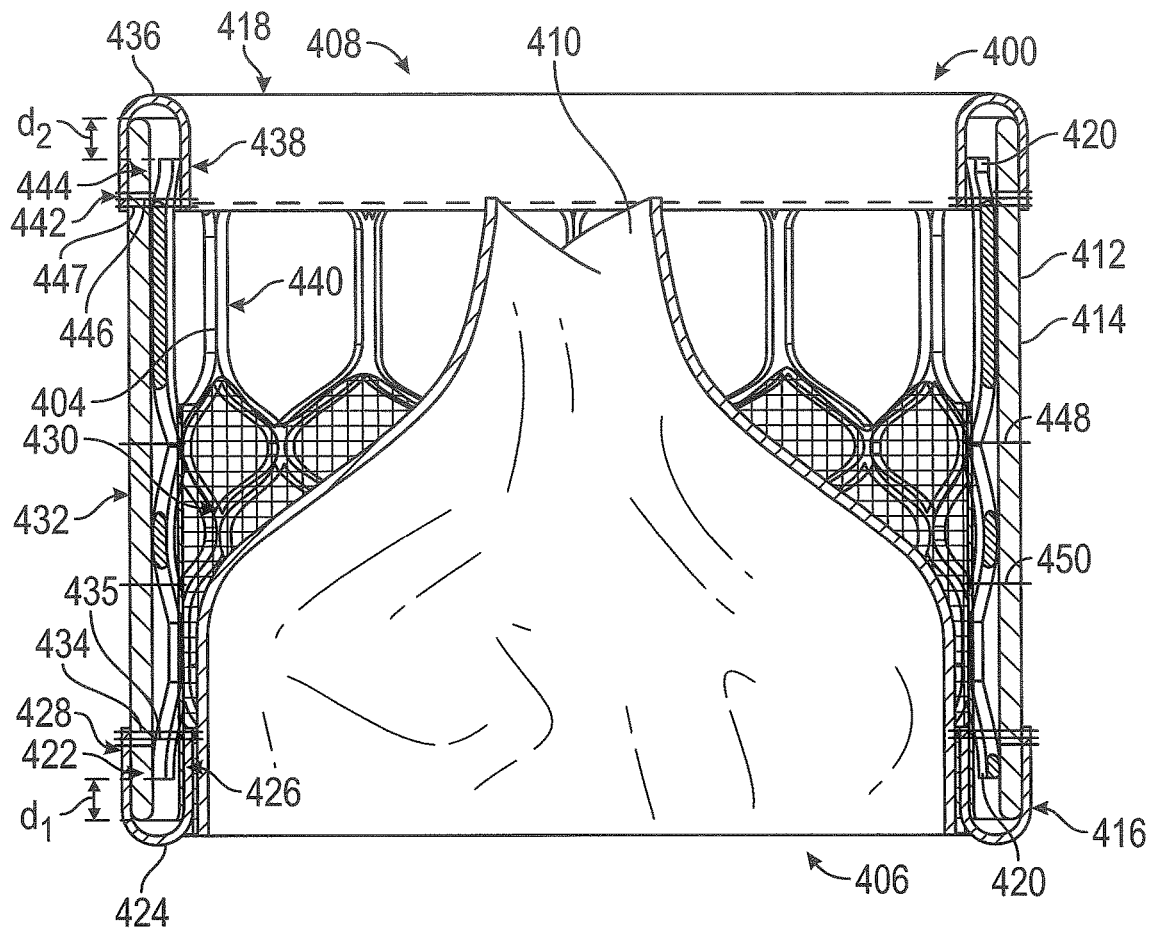
FIG. 22 is a cross-sectional side elevation view of the prosthetic heart valve of FIG. 19.

For example, with reference to FIG. 22, the inflow protective portion 416 can comprise a member configured as a strip 424 of material including a first circumferential edge portion 426 and a second circumferential edge portion 428. The strip member 424 of material can be folded such that the first circumferential edge portion 426 is adjacent (e.g., contacting) an inner skirt 430 disposed within the frame 402. The first circumferential edge portion 426 thereby forms a first or inner layer of the inflow protective portion 416. The strip member 424 can extend over the apices 420 of the strut members, and over an inflow end portion 422 of the cushioning layer 414 such that the second circumferential edge portion 428 is disposed on the exterior surface 432 of the cushioning layer 414. In this manner, the inflow end portion 422 of the cushioning layer 414 can form a second layer of the inflow protective portion 414, and the second circumferential edge portion 428 can form a third or outer layer of the inflow protective portion. The first and second circumferential edge portions 426, 428 of the strip member 424 can be secured to the strut members 404 (e.g., the rung of struts nearest the inflow end 406) with sutures 434, 435. Thus, the strip member 424 can encapsulate the apices 420, along with the inflow end portion 422 of the cushioning layer 414, between the first and second circumferential edge portions 426, 428.

In the illustrated configuration, the inflow protective portion 416 can extend beyond the apices 420 of the frame, similar to the embodiments above. In particular, the inflow end portion 422 of the cushioning layer 414 can extend beyond the apices 420 of the frame and into the inflow protective portion 416 within the folded strip 424. In this manner, the inflow end portion 422 of the cushioning layer 414, together with the strip member 424, can impart a resilient, cushioning quality to the inflow protective portion 416. This can also allow the inflow protective portion 416 to resiliently deform to accommodate and protect, for example, native tissue, other implants, etc., that come in contact with the inflow protective portion.

In the illustrated embodiment, the inflow end portion 422 can extend beyond the apices 420 by a distance $d_1$. The distance $d_1$ can be configured such the inflow end portion 422 can extend over or cover the apices 420 when the inflow protective portion 416 comes in contact with, for example, native tissue at the treatment site. The strip member 424 can also form a dome over the edge of the of the inflow end portion 422 such that the edge of the inflow end portion 422 is spaced apart from the domed portion of the strip member 424. In other embodiments, the strip member 424 can be folded such that it contacts the edge of the inflow edge portion 422, similar to the embodiment of FIG. 13.

The outflow protective portion 418 can include a member configured as a strip 436 of material folded such that a first circumferential edge portion 438 is adjacent (e.g., contacting) inner surfaces 440 of the strut members, and a second circumferential edge portion 442 is disposed on the exterior surface 432 of the cushioning layer 414, similar to the inflow protective portion 416. An outflow end portion 444 of the cushioning layer 414 can extend beyond the apices 420 by a distance $d_2$, and can be encapsulated by the strip member 436 together with the apices 420 between the first and second circumferential edge portions 438, 442. The distance $d_2$ can be the same as distance $d_1$ or different, as desired. The strip member 436 can be secured to the strut members 404 with sutures 446, 447. The strip member 436 can also form a domed shape similar to the strip member 424.

In certain configurations, the cushioning layer 414 can be a fabric including a plush pile, such as a velour fabric, or any other type of plush knitted, woven, or non-woven material, as described above. In some embodiments, the cushioning layer 414 may also comprise a relatively low thickness woven fabric without a plush pile. In certain configurations, the strip members 424, 436 can be made of resilient natural tissue materials such as pericardium. Alternatively, the strip members can also be made from fabric or polymeric materials such as PTFE or ePTFE.

Figure 23:
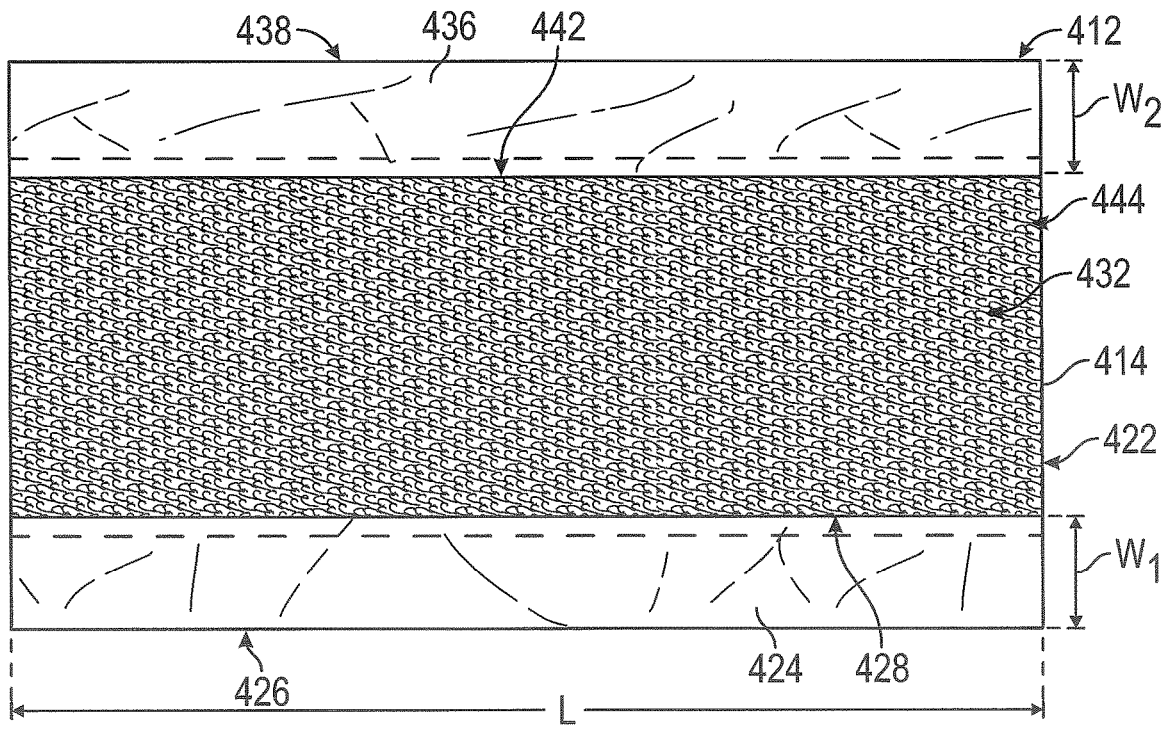
FIG. 23 is a top plan view of the covering of FIG. 19 in an unfolded configuration.

FIGS. 23-26 illustrate a representative method of making the outer covering 412 and attaching the covering to the prosthetic valve 400 to form the inflow and outflow protective portions 416, 418. FIG. 23 illustrates the outer covering 412 in an unfolded configuration prior to securing the covering to the frame 402. As illustrated in FIG. 23, the second circumferential edge portion 428 of the strip member 424 can be sutured to the plush surface 432 (e.g., the first surface) of the cushioning layer 414 at the inflow end portion 422 of the cushioning layer. The second circumferential edge portion 442 of the strip member 436 can be sutured to the plush surface 432 of the cushioning layer 414 at the outflow end portion 444 of the cushioning layer.

In the illustrated configuration, the cushioning layer 414 and the strip members 424, 436 can have a length dimension L corresponding to a circumference of the frame 402. In a representative example, the length dimension L can be about 93 mm. The strip members 424, 436 can also have respective width dimensions $W_1$, $W_2$. Referring to width dimension $W_1$ for purposes of illustration, the width dimension $W_1$ can be configured such that the strip member 424 extends from the interior of the valve to the exterior of the valve without contacting the apices 420 of the strut members, as shown in FIG. 22. For example, the width dimension $W_1$ can be configured such that the strip member 424 extends from adjacent the rung of strut members 404 at the inflow end 406 of the frame to the exterior of the valve adjacent the same rung of strut members and forms a domed shape over the apices 420. In certain configurations, the width dimension $W_1$ can be about 6 mm. The width dimension $W_2$ can be the same as $W_1$ or different, as desired.

Figure 24:
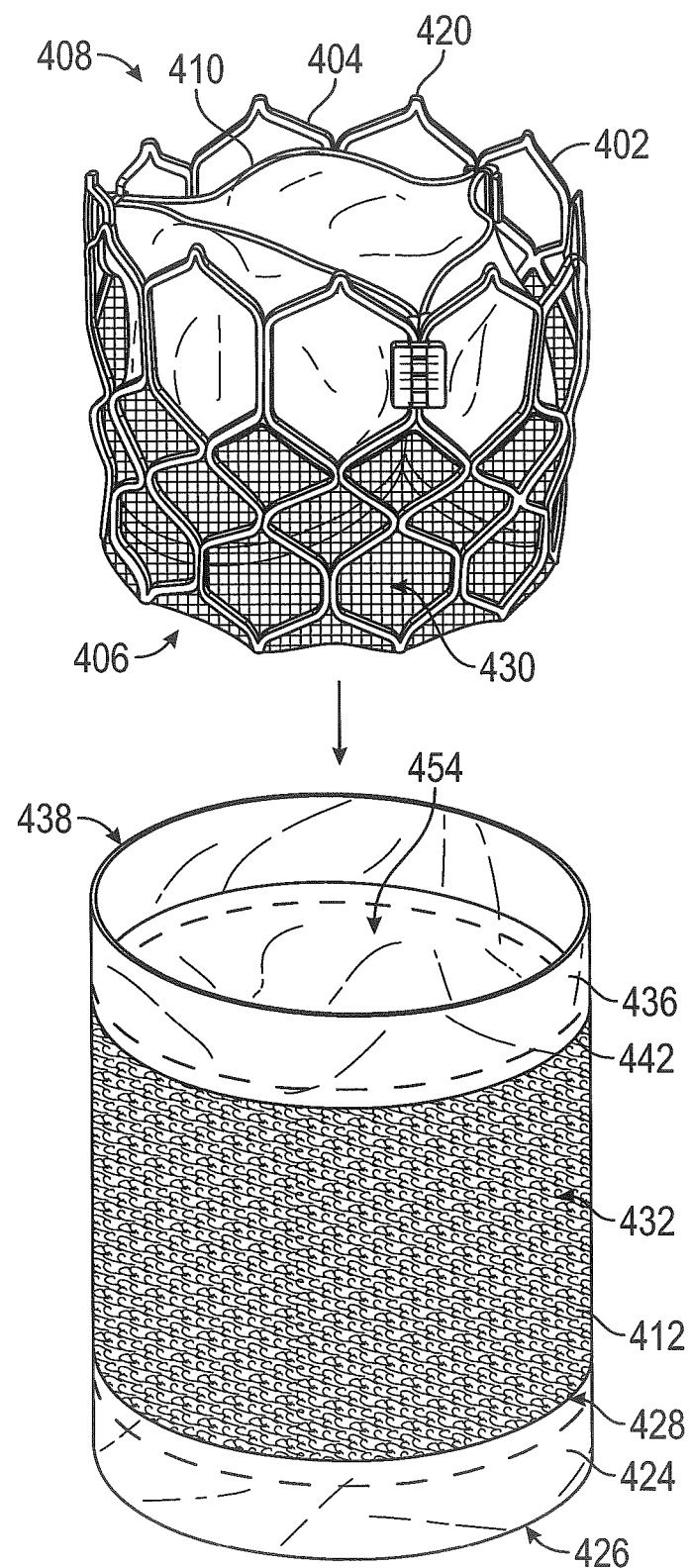
FIG. 24 is a perspective view illustrating placement of the prosthetic heart valve of FIG. 19 into the covering after the covering is formed into a cylindrical shape.

Referring to FIG. 24, the outer covering 412 can be folded and sutured into a cylindrical shape. The outer covering 412 can then be situated around the frame 402 such that a second or interior surface 454 of the cushioning layer 414 is oriented toward the frame. In certain configurations, the frame 402 can already include the inner skirt 430 and the leaflet structure 410, as shown in FIG. 24.

Figure 25:
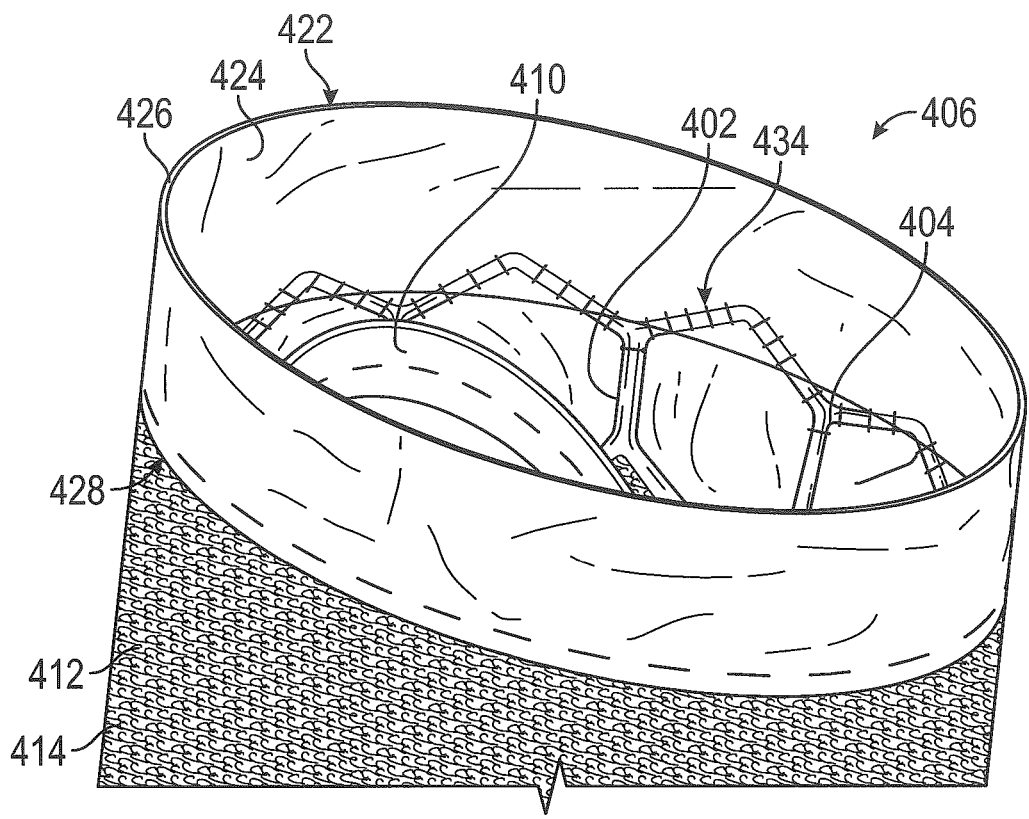
FIG. 25 is a perspective view of the inflow end of the prosthetic heart valve of FIG. 19 illustrating attachment of the covering to the strut members of the valve frame.
Figure 26:
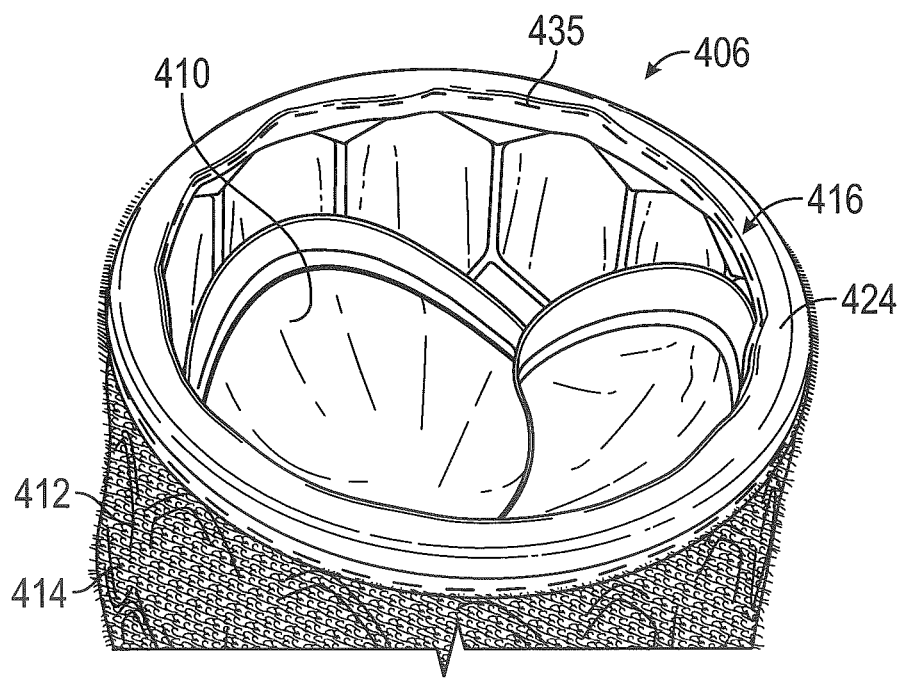
FIG. 26 is a perspective view of the inflow end of the prosthetic heart valve of FIG. 19 illustrating a strip member of the covering folded over the strut members of the valve frame to form an inflow protective portion.

Referring to FIGS. 25 and 26, the outer covering 412 can then be sutured to the frame. For example, as illustrated in FIG. 25, the strip member 424 can be aligned with an adjacent rung of strut members 404 (e.g., the rung of strut members nearest the inflow end of the frame). The cushioning layer 414 and/or the strip member 424 can then be sutured to the strut members 404 at suture line 434. The strip member 424 can then be folded over the apices 420 at the inflow end of the frame, and the first and second circumferential edge portions 426, 428 can be sutured to each other at suture line 435 to form the inflow protective portion 416. In other embodiments, the strip member 424 can be folded and sutured to form the inflow protective portion 416 before the outer covering 412 is sutured to the frame.

The outflow protective portion 418 can be formed in a similar manner. For example, the strip member 426 can be aligned with the rung of strut members 404 adjacent the outflow end 408 of the frame, and the strip member 426 and/or the cushioning layer 414 can be sutured to the strut members. The strip member 436 can then be folded over the apices 420 and the cushioning layer 414 at the outflow end of the frame, and the first and second circumferential edge portions 438, 442 can be sutured together, and to the rung of strut members 404 adjacent the outflow end of the frame, to form the outflow protective portion 418. The covering 412 can also be sutured to the frame at one or more additional locations, such as at suture lines 448 and 450, as shown in FIG. 22.

Figure 27:
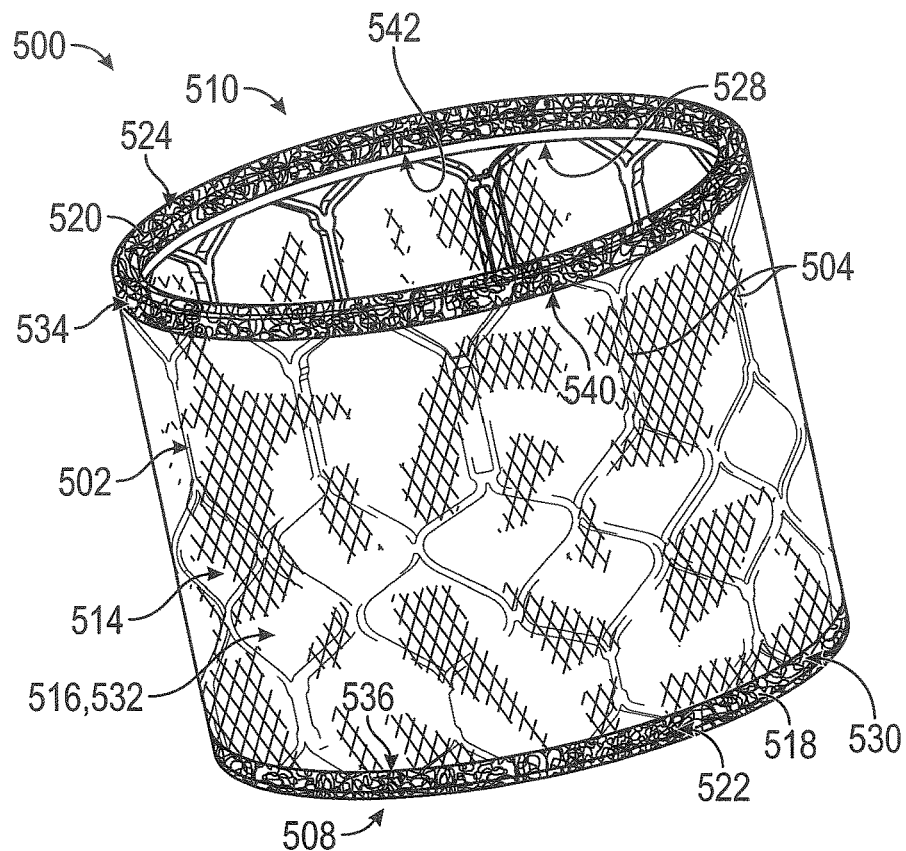
FIG. 27 is a perspective view of a frame for a prosthetic heart valve including another embodiment of a covering.
Figure 28:
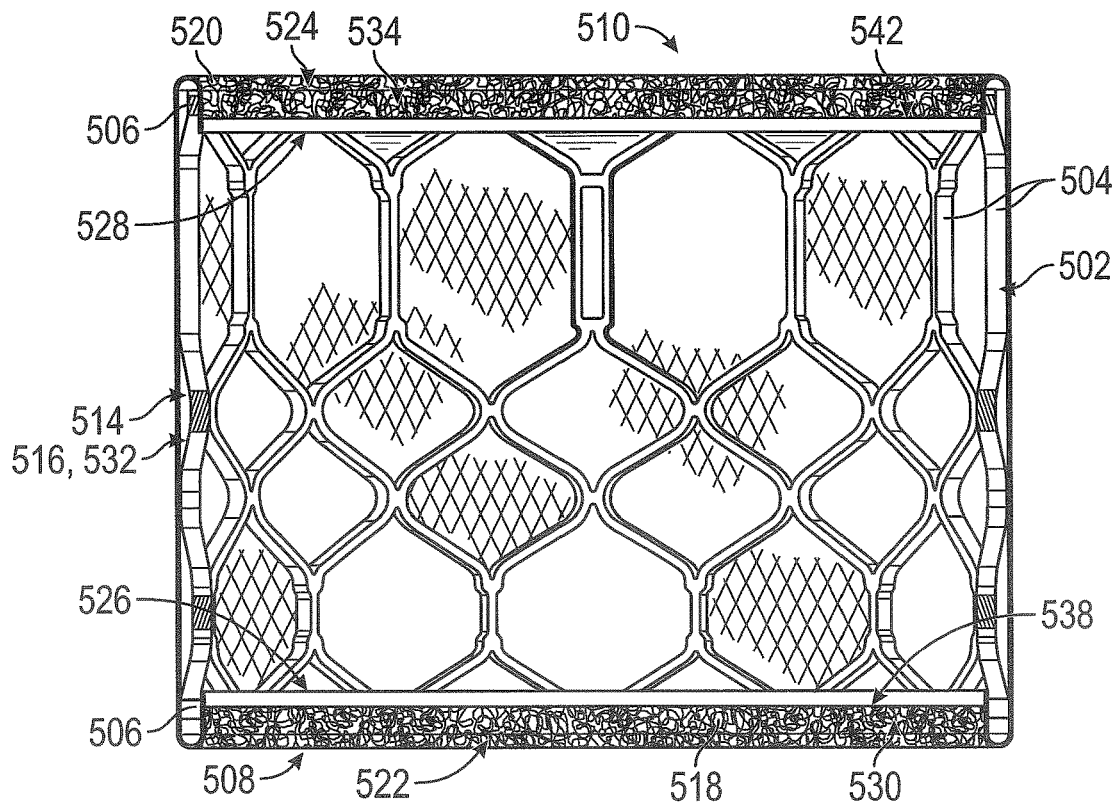
FIG. 28 is a cross-sectional side elevation view of the frame and covering of FIG. 27.

FIGS. 27 and 28 illustrates another embodiment of a prosthetic heart valve 500 including a frame 502 formed by a plurality of strut members 504 defining apices 506 (FIG. 28), similar to the frame 102 described above and in U.S. Pat. No. 9,393,110. The prosthetic valve 500 can have an inflow end 508 and an outflow end 510, and can include a leaflet structure (not shown) situated at least partially within the frame.

The prosthetic valve can include an outer covering 514 situated about the frame 502. The outer covering 514 can include a main cushioning layer 516 (also referred to as a main layer) having a cylindrical shape, and made from a woven, knitted, or braided fabric (e.g., a PET fabric, an ultra-high molecular weight polyethylene (UHMWPE) fabric, a PTFE fabric, etc.). In some embodiments, the fabric of the main cushioning layer 516 can include a plush pile. In some embodiments, the fabric of the main cushioning layer 516 can comprise texturized yarns in which the constituent fibers of the yarns have been bulked by, for example, being twisted, heat set, and untwisted such that the fibers retain their deformed, twisted shape and create a voluminous fabric. The volume contributed by the texturized yarns can improve the cushioning properties of the covering, as well as increase friction between the fabric and the surrounding anatomy and/or an anchoring device into which the valve is deployed.

The outer covering 514 can include an inflow protective portion 518 extending circumferentially around the inflow end 508 of the frame, and an outflow protective portion 520 extending circumferentially around the outflow end 510 of the frame. In certain embodiments, the inflow and outflow protective portions 518 and 520 can be formed on the fabric of the main cushioning layer 516 such that the outer covering 514 is a one-piece, unitary construction, as described further below.

Referring to FIG. 28, the main cushioning layer 516 can include a first circumferential edge portion 522 (also referred to as an inflow edge portion) located adjacent the inflow end 508 of the valve, which can form a part of the inflow protective portion 518. The cushioning layer 516 can further include a second circumferential edge portion 524 (also referred to as an outflow edge portion) located adjacent the outflow end 510 of the valve, and which can form a part of the outflow protective portion 520. Referring still to FIG. 28, the first circumferential edge portion 522 can comprise an edge 526, and the second circumferential edge portion 524 can comprise an edge 528. The first circumferential edge portion 522 can be folded or wrapped over the apices 506 of the strut members 504 such that the edge 526 is disposed on the inside of the frame 502. The second circumferential edge portion 524 can be folded around the apices 506 at the outflow end 510 of the frame in a similar fashion such that the edge 528 is also disposed on the inside of the frame opposite the edge 522.

In the illustrated configuration, the inflow protective portion 518 can include a second or outer layer configured as a lubricious layer 530 of material disposed on an outer surface 532 of the main cushioning layer 516. The outflow protective portion 520 can also include a second or outer lubricious layer 534 of material disposed on the outer surface 532 of the main cushioning layer 516. In some embodiments, the layers 530 and 534 can be smooth, low-thickness coatings comprising a low-friction or lubricious material. For example, in certain configurations one or both of the layers 530, 534 can comprise PTFE or ePTFE.

In the illustrated configuration, the lubricious layer 530 can have a first circumferential edge 536 (FIG. 27) and a second circumferential edge 538 (FIG. 28). The lubricious layer 530 can extend from the outer surface 532 of the main cushioning layer 516 and over the apices 506 such that the first circumferential edge 536 is disposed on the outside of the frame and the second circumferential edge 538 is disposed on the inside of the frame. The lubricious layer 534 can be configured similarly, such that a first circumferential edge 540 (FIG. 27) is disposed outside the frame, the layer 534 extends over the apices 506 of the outflow end 510 of the frame, and a second circumferential edge 542 (FIG. 28) is disposed inside the frame. Once implanted in a native heart valve, the protection portions 518 and 520 can prevent direct contact between the apices 506 and the surrounding anatomy. The lubricious material of the layers 530 and 534 can also reduce friction with tissue of the native valve (e.g., chordae) in contact with the inflow and outflow ends of the prosthetic valve, thereby preventing damage to the tissue. In other embodiments, the entire outer surface 532 of the main cushioning layer 516, or a portion thereof, can be covered with a lubricious coating such as ePTFE in addition to the inflow and outflow protective portions 518 and 520 such that the lubricious coating extends axially from the inflow end to the outflow end of the covering. In yet other embodiments, the cushioning layer 516 can be formed from woven, knitted, braided, or electrospun fibers of lubricious material, such as PTFE, ePTFE, etc., and can form the inflow and outflow protective portions.

Figure 29:
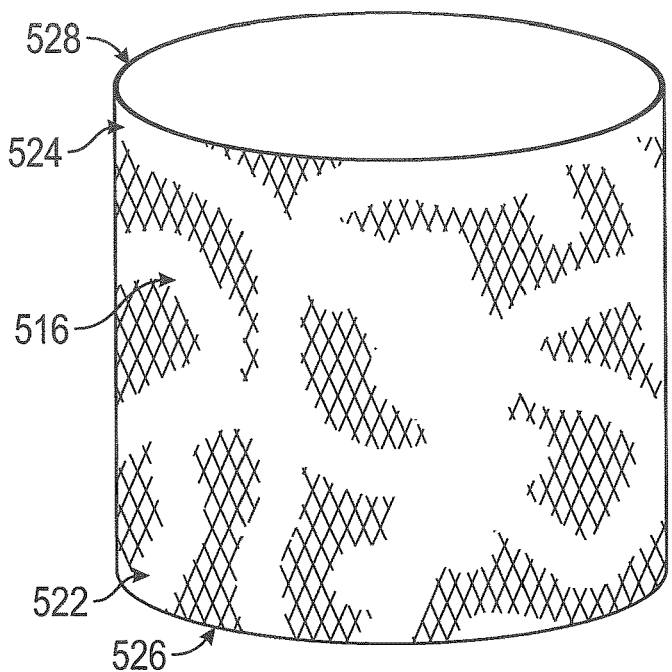
Figure 30:
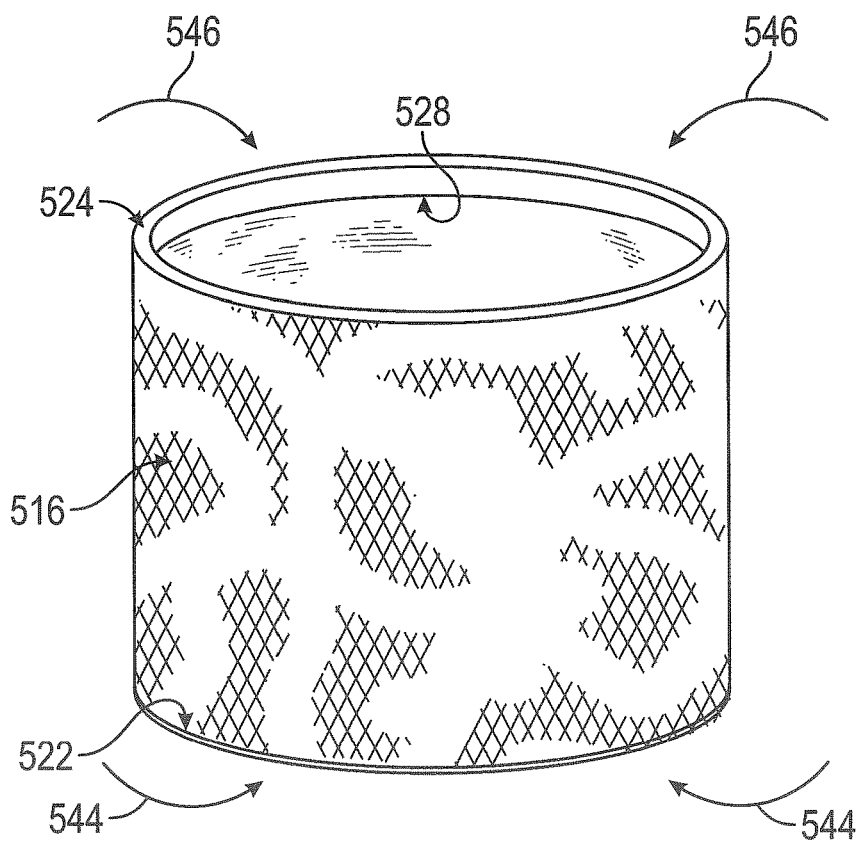

FIGS. 29-31B illustrate a representative method of making the covering 514. FIG. 29 illustrates the main cushioning layer 516 formed into a cylindrical, tubular body. Referring to FIG. 30, the first circumferential edge portion 522 of the cushioning layer 516 can then be folded over (e.g, inward toward the interior surface of the tubular body) in the direction of arrows 544 such that the lower edge 526 is inside the tubular body and disposed against the interior surface of the tubular body. The edge portion 524 can be folded in a similar manner as indicated by arrows 546 such that the top edge 528 is inside the tubular body and disposed against the interior surface.

Figure 31A:
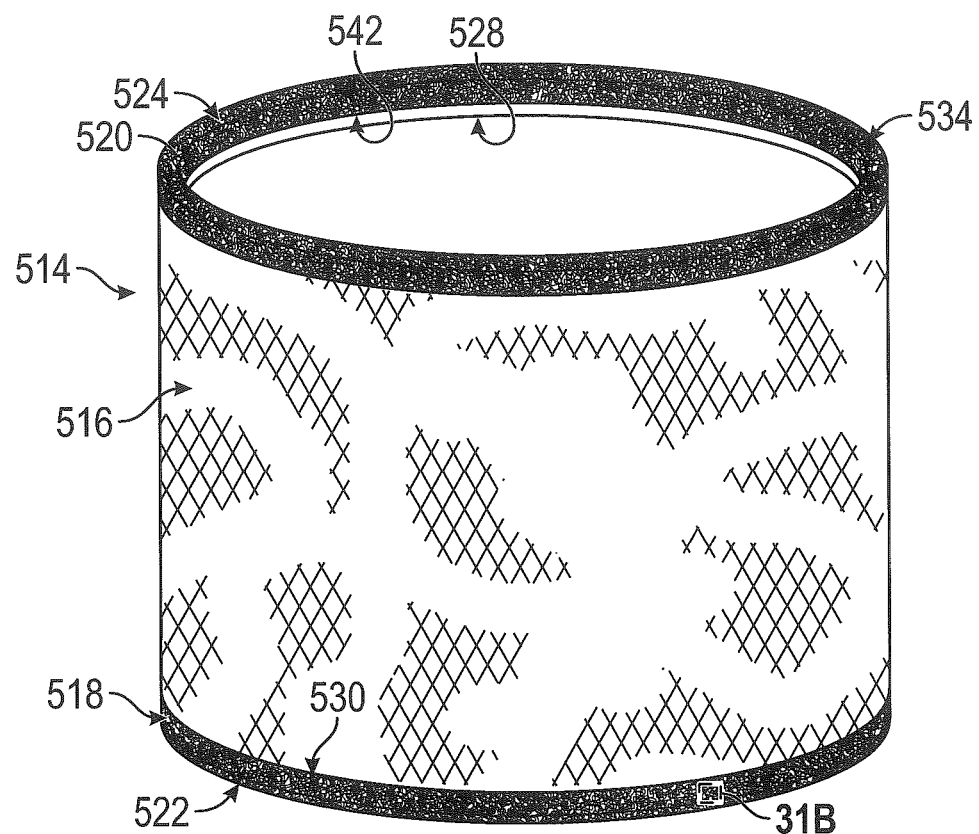
Figure 31B:
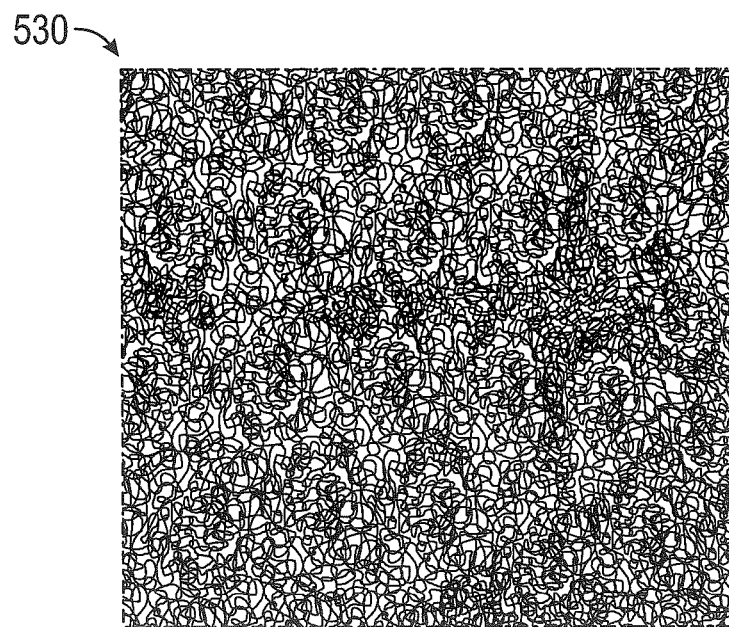
FIG. 31B is a detail view of the electrospun layer of the inflow end portion of the covering of FIG. 31A.

Referring to FIGS. 31A and 31B, the lubricious layers 530, 534 can then be applied to the main layer 516 to form the inflow and outflow protection portions 518 and 520. In certain embodiments, the lubricious layers 530, 534 can be formed by electrospinning a low-friction material (e.g., PTFE, ePTFE, etc.) onto the first and second circumferential edge portions 522 and 524. In certain embodiments, forming the layers 530, and 534 by electrospinning can provide a smooth, uniform surface, and keep the thickness of the layers within strictly prescribed specifications.

For example, the layers 530 and 534 can be made relatively thin, which can reduce the overall crimp profile of the valve. In certain embodiments, a thickness of the layers 530 and 534 can be from about 10 µm to about 500 µm, about 100 µm to about 500 µm, about 200 µm to about 300 µm, about 200 µm, or about 300 µm. In other embodiments, the layer 530 and/or 534 can be made by dip-coating, spray-coating, or any other suitable method for applying a thin layer of lubricious material to the main cushioning layer 516. The finished outer covering 514 can then be situated about and secured to the frame 502 using, for example, sutures, ultrasonic welding, or any other suitable attachment method. In other embodiments, the main cushioning layer 516 can be situated about the frame 502 before the edges are folded, and/or before the lubricious layers 530 and 534 are applied. In yet other embodiments, one or both of the lubricious layers 530 and/or 534 can be omitted from the first and second circumferential edge portions 522 and 524. In yet other embodiments, one or both of the first and second circumferential edge portions 522, 524 need not be folded inside the frame, but may extend to the respective inflow or outflow end of the frame, or beyond the ends of the frame on the exterior of the frame, as desired.

In addition to covering the frame 502 and the apices 506, the outer covering 514 can provide a number of other significant advantages. For example, the covering 514 can be relatively thin, allowing the prosthetic valve to achieve a low crimp profile (e.g., 23 Fr or below). The one-piece, unitary construction of the outer covering 514 and the protective portions 518 and 520 can also significantly reduce the time required to produce the covering and secure it to the frame, and can increase production yield.

In some embodiments, one or both of the inflow and outflow protection portions can be configured as separate coverings that are spaced apart from the main outer covering, and may or may not be coupled to the main outer covering. For example, FIGS. 32-36 illustrate another embodiment of a prosthetic heart valve 600 including a frame 602 formed by a plurality of strut members 604 defining apices 606, similar to the frame 102 described above and in U.S. Pat. No. 9,393,110. The prosthetic valve 600 can have an inflow end 608 and an outflow end 610, and can include a plurality of leaflets 612 situated at least partially within the frame.

Figure 34:
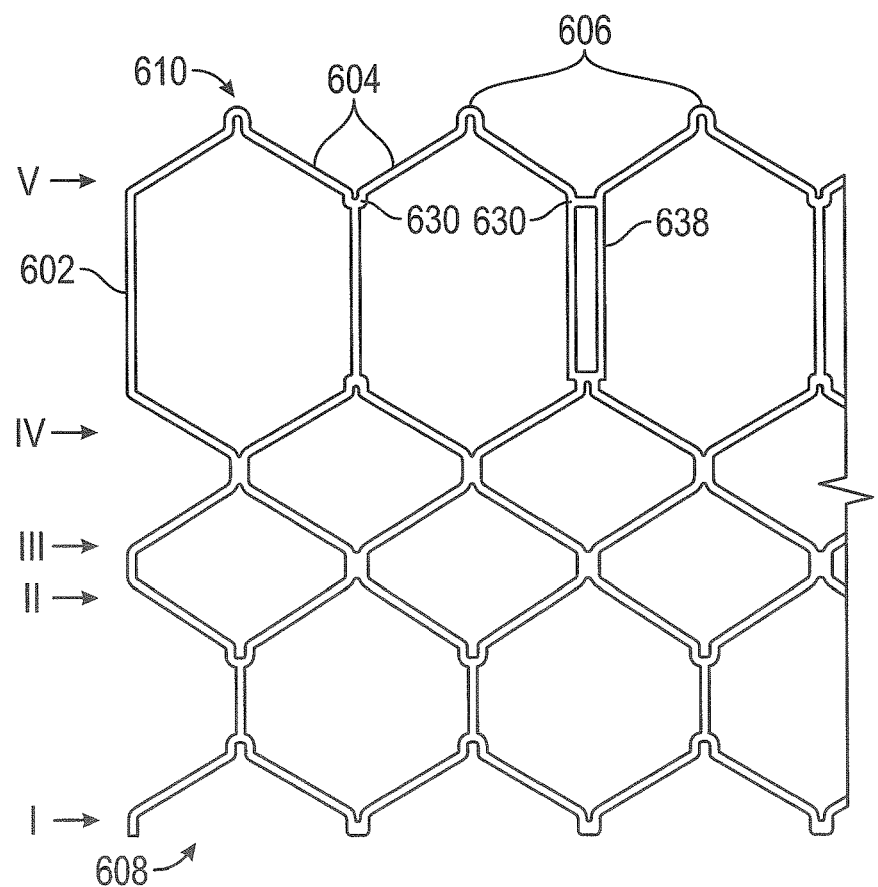
FIG. 34 is a plan view of a portion of the frame of the prosthetic valve of FIG. 32 in a laid-flat configuration.

FIG. 34 illustrates a portion of the frame 602 in a laid-flat configuration for purposes of illustration. The strut members 604 can be arranged end-to-end to form a plurality of rows or rungs of strut members that extend circumferentially around the frame 602. For example, with reference to FIG. 34, the frame 602 can comprise a first or lower row I of angled strut members forming the inflow end 608 of the frame; a second row II of strut members above the first row; a third row III of strut members above the second row; a fourth row IV of strut members above the third row, and a fifth row V of strut members above the fourth row and forming the outflow end 610 of the frame. At the outflow end 610 of the frame, the strut members 604 of the fifth row V can be arranged at alternating angles in a zig-zag pattern. The strut members 604 of the fifth row V can be joined together at their distal ends (relative to the direction of implantation in the mitral valve) to form the apices 606, and joined together at their proximal ends at junctions 630, which may form part of the commissure windows 638. Additional structure and characteristics of the rows I-V of strut members 604 are described in greater detail in U.S. Pat. No. 9,393,110, incorporated by reference above.

Returning to FIGS. 32 and 33, the prosthetic valve can include a first covering 614 (also referred to as a main covering) situated about the frame 602. The valve can also include an outflow protective portion configured as a second covering 616 disposed about the strut members 604 and the apices 606 of the fifth row V of strut members at the outflow end 610 of the frame. The first covering 616 can comprise a woven or knitted fabric made from, for example, PET, UHMWPE, PTFE, etc. Referring to FIG. 33, the first covering 614 can include an inflow end portion 618 located at the inflow end 608 of the valve, and an outflow end portion 620 located at the outflow end 610 of the valve. In the illustrated embodiment, the outflow end portion 620 of the first covering 614 can be offset toward the inflow end of the frame (e.g., in the upstream direction) from the fifth row V of strut members 604. Stated differently, the strut members 604 of the fifth row V can extend beyond an uppermost circumferential edge 622 of the first covering 614 (e.g., distally beyond the edge 622 when the prosthetic valve is implanted in the mitral valve). A lowermost circumferential edge 624 of the main covering 614 can be disposed adjacent the first row I of strut members 604 at the inflow end 608 of the valve. In some embodiments, the first covering 614 can extend over and cover the apices 606 at the inflow end 608 of the frame.

Figure 35:
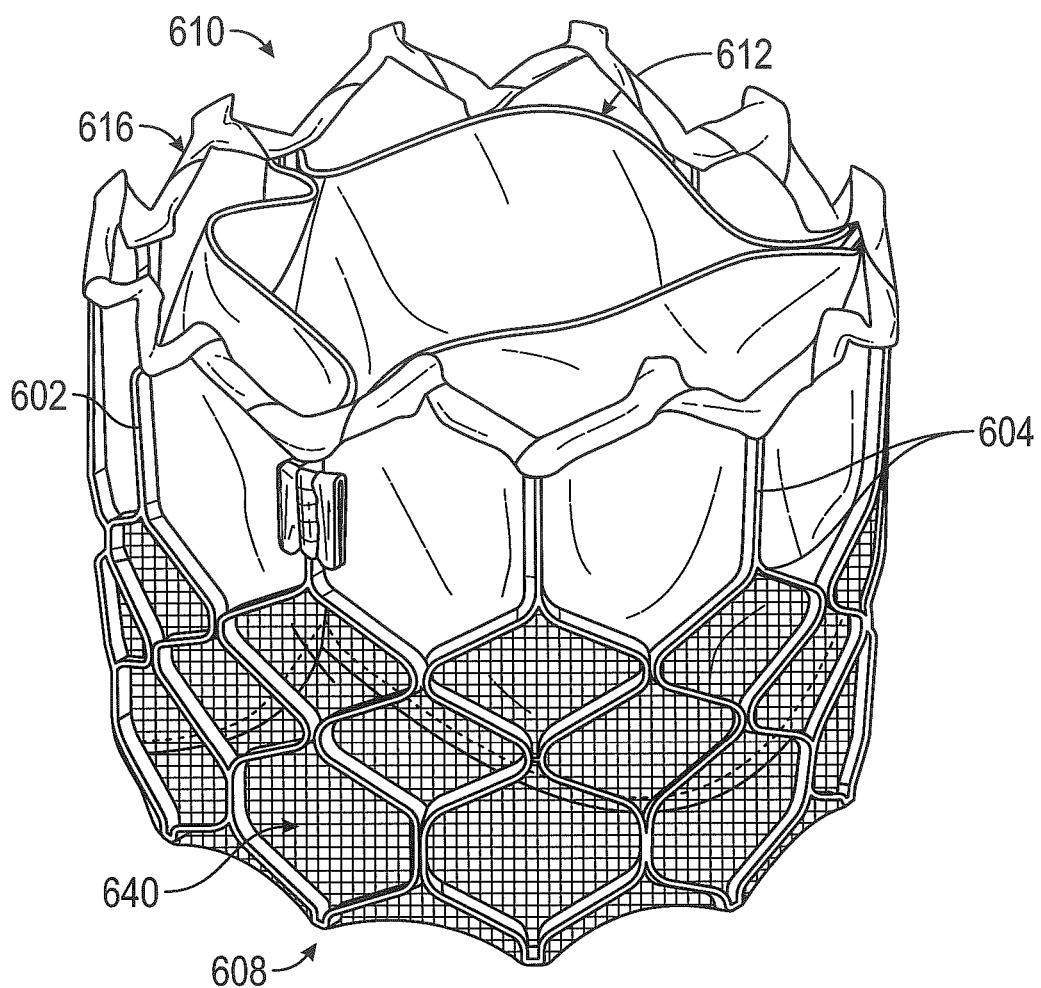
FIG. 35 is a perspective view of the prosthetic heart valve of FIG. 32 without the main outer covering.
Figure 36:
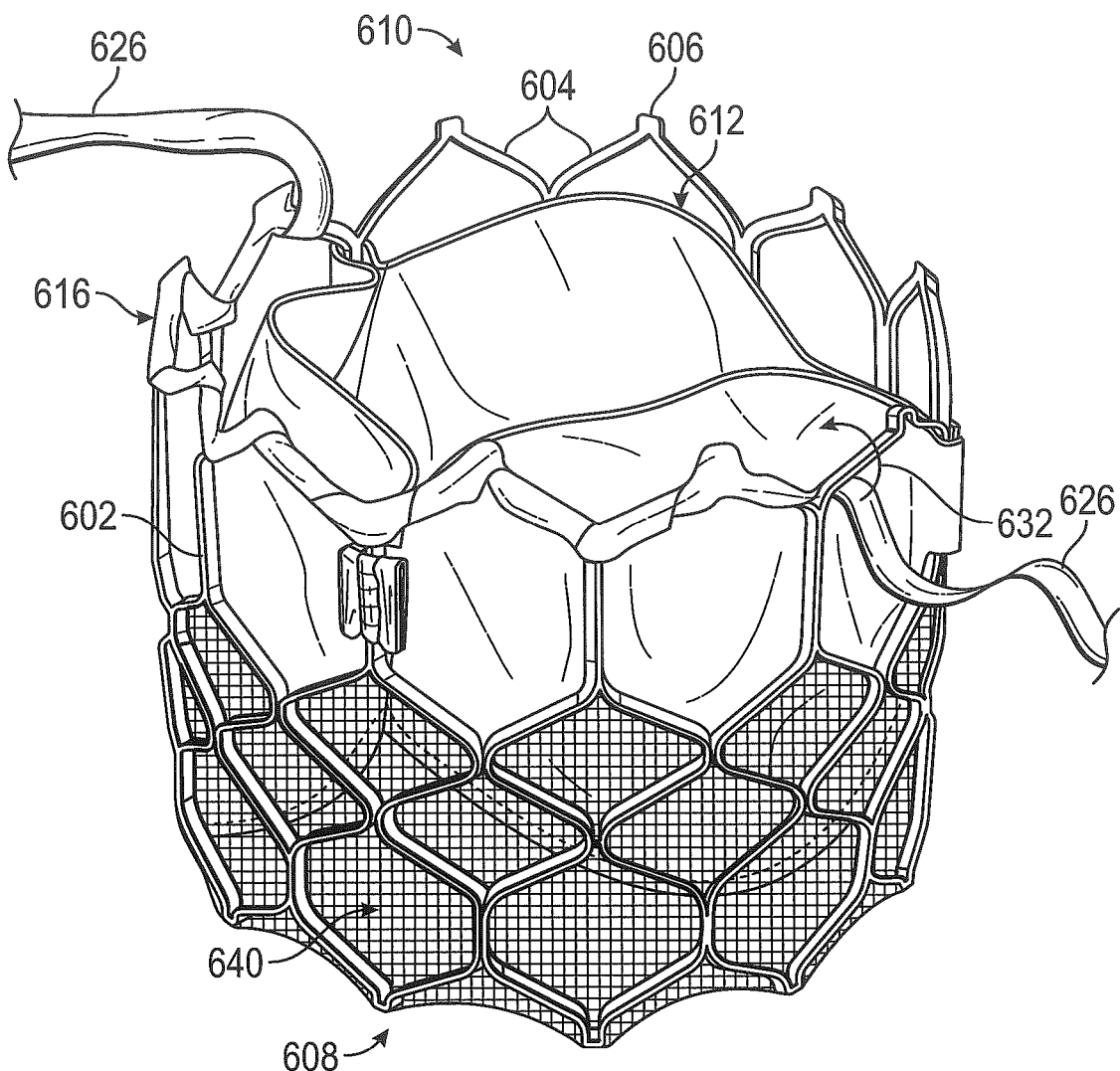
FIG. 36 is a perspective view of the prosthetic heart valve of FIG. 32 illustrating how the second covering is wrapped around the apices of the frame.

FIG. 35 illustrates the frame 602 including the second covering 616 and an inner skirt 640, and without the first covering 614 for purposes of illustration. In certain embodiments, the second covering 616 can be configured as a wrapping that extends around the circumference of the frame 602 and surrounds the fifth row V of strut members 604. For example, with reference to FIG. 36, the covering 616 can be configured as one or more straps or strips 626 of material that are helically wrapped around the struts 604 and the apices 606 of the fifth row V of strut members at the outflow end 610 of the frame in the direction such as indicated by arrow 632. In certain configurations, second covering 616 can be made of a lubricious or low-friction polymeric material, such as PTFE, ePTFE, UHMWPE, polyurethane, etc. In this manner, the second covering 616 can reduce friction between the second covering and native tissue that is in contact with the outflow end 610 of the valve. The covering 616 can also prevent injury to native tissue by preventing it from directly contacting the apices 606.

In some embodiments, the strip 626 can be relatively thick to improve the cushioning characteristics of the second covering 616. For example, in some embodiments, the strip 626 can be a PTFE strip having a thickness of from about 0.1 mm to about 0.5 mm, and a width of from about 3 mm to about 10 mm. In a representative embodiment, the strip 626 can have a thickness of about 0.25 mm, and a width of about 6 mm. The second covering 616 can also include one or multiple layers. For example, the second covering 616 can include a single layer (e.g., a single strip 626) wrapped around a row of struts of the frame. The second covering may also include two layers, three layers, or more of strips wrapped around a row of struts of the frame. In some embodiments, the second covering 616 can comprise multiple layers made of different materials. In certain configurations, the second covering 616 can also be porous, and can have a pore size and pore density configured to promote tissue ingrowth into the material of the second covering.

In some embodiments, the first covering 614 and/or the second covering 616 can be secured to the frame by, for example, suturing. In some embodiments, the first and second coverings 614, 616 can also be secured to each other. For example, with reference to FIGS. 32 and 33, the first covering 614 can include one or more sutures 628 extending circumferentially around the outflow end portion 620 of the first covering in, for example, a running stitch. At or near the junctions 630 (FIG. 34) of the fifth row V of strut members 604, the suture 628 can extend out of the stitch line (e.g., from the radially outward surface of the covering 614), and loop over the second covering 616. The suture 628 can then reenter the covering 614 (e.g., on the radially inward surface of the covering 614) and resume the running stitch. In the illustrated embodiment, the suture 628 can loop over the second covering 616 at the junctions 630. The loops of suture 628 thereby rest in "valleys" between the apices 606, and can serve to hold the second covering 616 in place on the strut members 602. The suture 628 can also hold the first covering 614 in place while the valve is being crimped.

Figure 32:
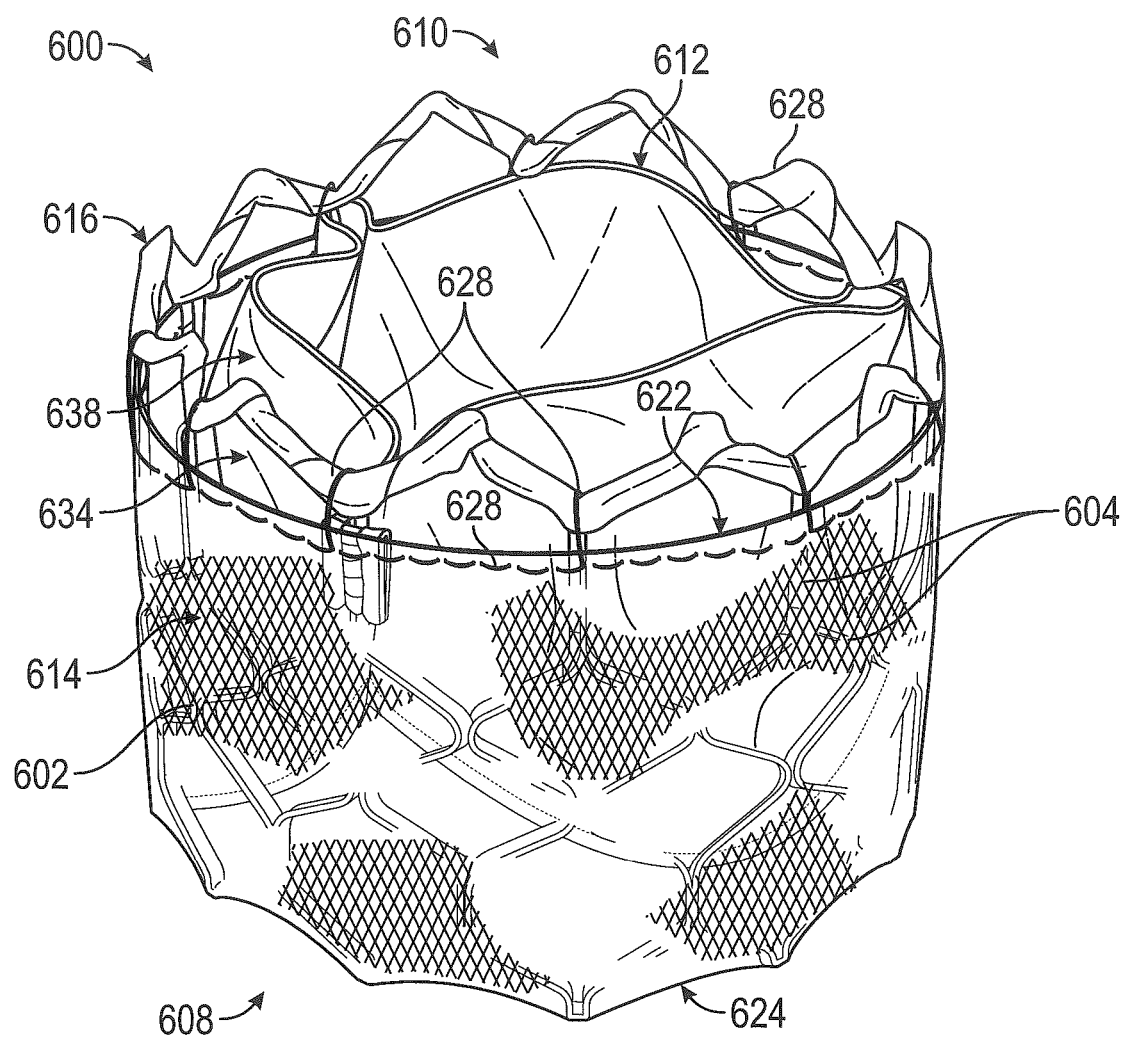
FIG. 32 is a perspective view of a prosthetic heart valve including a main covering and a second covering extending over the apices of the frame.
Figure 33:
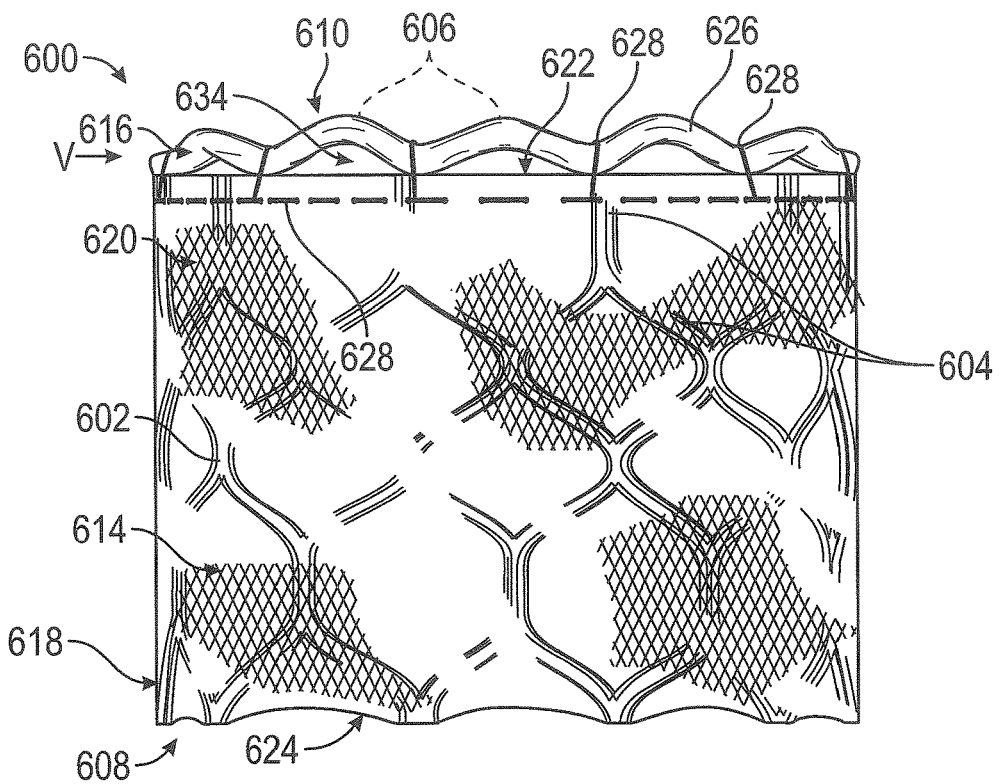
FIG. 33 is a side elevation view of the prosthetic heart valve of FIG. 32.

Still referring to FIGS. 32 and 33, the circumferential edge 622 of the first covering 614 can be relatively straight, while the second covering 616 can conform to the angled or zig-zag pattern of the fifth row V of strut members 604. In this manner, the first and second coverings 614 and 616 can define a plurality of gaps or openings 634 through the frame 602 between the first and second coverings. In the illustrated embodiment, the openings 634 have a triangular shape, with the base of the triangle being defined by the edge 622 of the first covering 614, and the sides being defined by the second covering 616. The openings 634 can be configured such that after the valve 600 is implanted, blood can flow in and/or out of the frame 602 through the openings. In this manner, the space between the interior of the frame 602 and the ventricular surfaces 638 of the leaflets 612 can be flushed or washed by blood flowing into and out of the openings 634 during operation of the prosthetic valve. This can reduce the risk of thrombus formation and left ventricular outflow tract obstruction.

Figure 37:
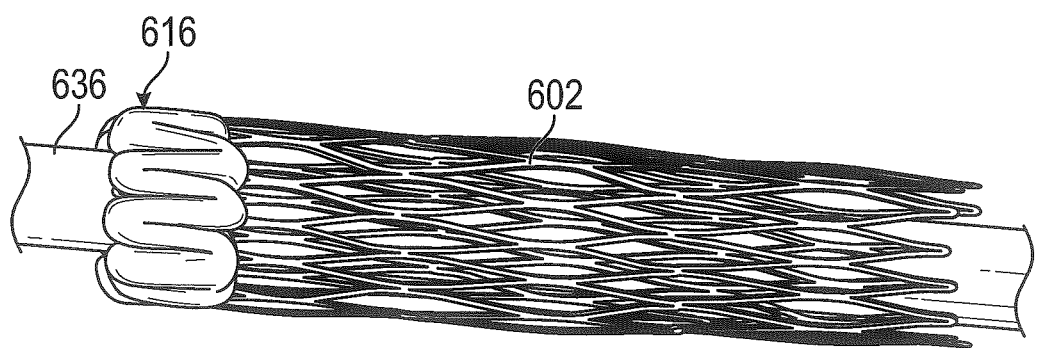
FIG. 37 is a perspective view illustrating the frame of the prosthetic valve of FIG. 32 including the second covering crimped onto a shaft of a delivery apparatus.

FIG. 37 illustrates the frame 602 including the second covering 616 in a radially collapsed or crimped delivery configuration on a shaft 636 of a delivery apparatus. As shown in FIG. 37, the second covering 616 can conform to the closely-packed, serpentine shape of the strut members 604 as they move to the radially collapsed configuration. In certain configurations, the second covering 616 can closely mimic the shape and direction of the strut members 604 without bulging, pleating, creasing, or bunching to maintain a low crimp profile. In other embodiments, the inflow end of the frame can also include a separate covering similar to the covering 616.

FIGS. 38A, 38B, 39A, and 39B illustrate the prosthetic valve 400 of FIGS. 19-26 including an outer covering 700, according to another embodiment. The outer covering 700 can include a main cushioning layer 702 having a plush exterior surface 704. The covering 700 can also include an inflow protection portion 706 extending circumferentially around the inflow end 406 of the valve, and an outflow protection portion 708 extending circumferentially around the outflow end 408 of the valve. As in the embodiment of FIGS. 19-26, the inflow and outflow protection portions 706, 708 can be formed with separate pieces of material that are folded around the circumferential ends of the main layer 702 such that the cushioning portions encapsulate the apices 420 of the strut members at the inflow and outflow ends of the valve. For example, the inflow and outflow protection portions 706, 708 can be constructed from strips of material (e.g., polymeric materials such as PTFE, ePTFE, etc., or natural tissues such as pericardium, etc.) folded such that one circumferential edge of the strips is disposed against the interior of the frame 402 (or an inner skirt within the frame), and the other circumferential edge is disposed against the outer surface of the main layer 702. The outer covering 700 can be secured to the frame 402 using, for example, sutures, ultrasonic welding, or any other suitable attachment method.

The main layer 702 of the outer covering 700 can comprise a woven or knitted fabric. The fabric of the main layer 702 can be resiliently stretchable between a first, natural, or relaxed configuration (FIGS. 38A and 38B), and a second, elongated, or tensioned configuration (FIGS. 39A and 39B). When disposed on the frame 402, the relaxed configuration can correspond to the radially expanded, functional configuration of the prosthetic valve, and the elongated configuration can correspond to the radially collapsed delivery configuration of the valve. Thus, with reference to FIG. 38A, the outer covering 700 can have a first length $L_1$ when the prosthetic valve is in the expanded configuration, and a second length $L_2$ (FIG. 39A) that is longer than $L_1$ when the valve is crimped to the delivery configuration, as described in greater detail below.

The fabric can comprise a plurality of circumferentially extending warp yarns 712 and a plurality of axially extending weft yarns 714. In some embodiments, the warp yarns 712 can have a denier of from about 1 D to about 300 D, about 10 D to about 200 D, or about 10 D to about 100 D. In some embodiments, the warp yarns 712 can have a thickness $t_1$ (FIG. 40A) of from about 0.01 mm to about 0.5 mm, about 0.02 mm to about 0.3 mm, or about 0.03 mm to about 0.1 mm. In some embodiments, the warp yarns 712 can have a thickness $t_1$ of about 0.03 mm, about 0.04 mm, about 0.05 mm, about 0.06 mm, about 0.07 mm, about 0.08 mm, about 0.09 mm, or about 0.1 mm. In a representative embodiment, the warp yarns 712 can have a thickness of about 0.06 mm.

The weft yarns 714 can be texturized yarns comprising a plurality of texturized filaments 716. For example, the filaments 716 of the weft yarns 714 can be bulked, wherein, for example, the filaments 716 are twisted, heat set, and untwisted such that the filaments retain their deformed, twisted shape in the relaxed, non-stretched configuration. The filaments 716 can also be texturized by crimping, coiling, etc. When the weft yarns 714 are in a relaxed, non-tensioned state, the filaments 716 can be loosely packed and can provide compressible volume or bulk to the fabric, as well as a plush surface. In some embodiments, the weft yarns 714 can have a denier of from about 1 D to about 500 D, about 10 D to about 400 D, about 20 D to about 350 D, about 20 D to about 300 D, or about 40 D to about 200 D. In certain embodiments, the weft yarns 714 can have a denier of about 150 D. In some embodiments, a filament count of the weft yarns 714 can be from 2 filaments per yarn to 200 filaments per yarn, 10 filaments per yarn to 100 filaments per yarn, 20 filaments per yarn to 80 filaments per yarn, or about 30 filaments per yarn to 60 filaments per yarn. Additionally, although the axially-extending textured yarns 714 are referred to as weft yarns in the illustrated configuration, the fabric may also be manufactured such that the axially-extending textured yarns are warp yarns and the circumferentially-extending yarns are weft yarns.

Figure 40A:
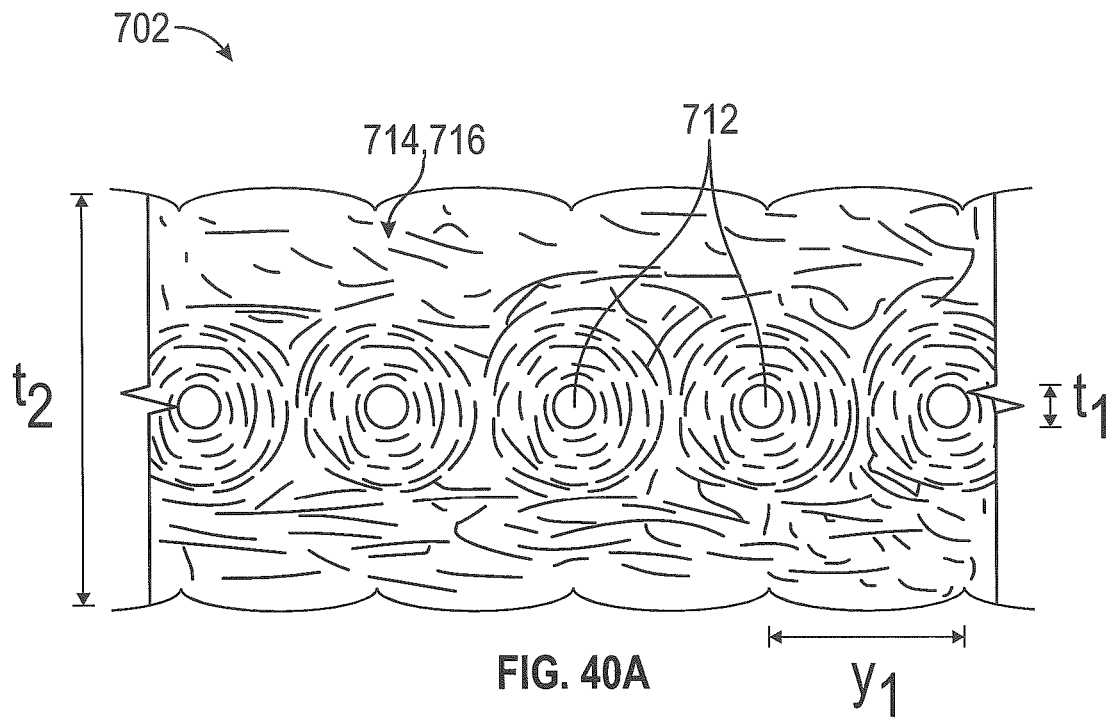
FIG. 40A is a cross-sectional side elevation view of the fabric of the outer covering of FIG. 38A in a relaxed state.
Figure 40B:
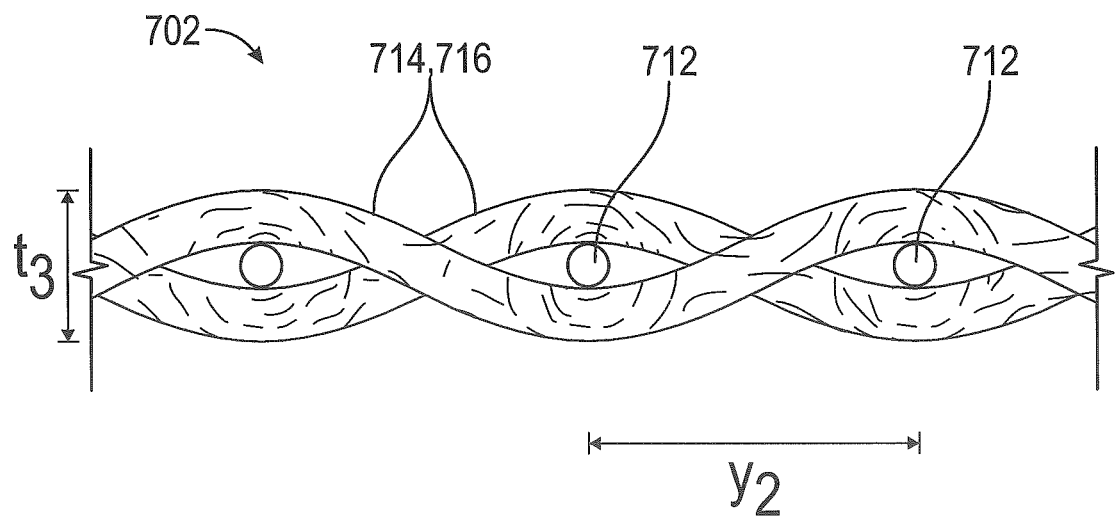
FIG. 40B is a cross-sectional side elevation view of the fabric of the outer covering of FIG. 38A in a tensioned state.

FIGS. 40A and 40B illustrate a cross-sectional view of the main layer 702 in which the weft yarns 712 extend into the plane of the page. With reference to FIG. 40A, the fabric of the main layer 702 can have a thickness $t_2$ of from about 0.1 mm to about 10 mm, about 1 mm to about 8 mm, about 1 mm to about 5 mm, about 1 mm to about 3 mm, about 0.5 mm, about 1 mm, about 1.5 mm, about 2 mm, about 2.5 mm, or about 3 mm when in a relaxed state and secured to a frame. In some embodiments, the main layer 702 can have a thickness of about 0.1 mm, about 0.2 mm, about 0.3 mm, about 0.4 mm, or about 0.5 mm as measured in a relaxed state with a weighted drop gauge having a presser foot. In a representative example, the main layer 702 can have a thickness of about 1.5 mm when secured to a prosthetic valve frame in the relaxed state. This can allow the fabric of the main layer 702 to cushion the leaflets between the valve body and an anchor or ring into which the valve is implanted, as well as to occupy voids or space in the anatomy. The texturized, loosely packed filaments 716 of the weft yarns 714 in the relaxed state can also promote tissue growth into the main layer 702.

Figure 38A:
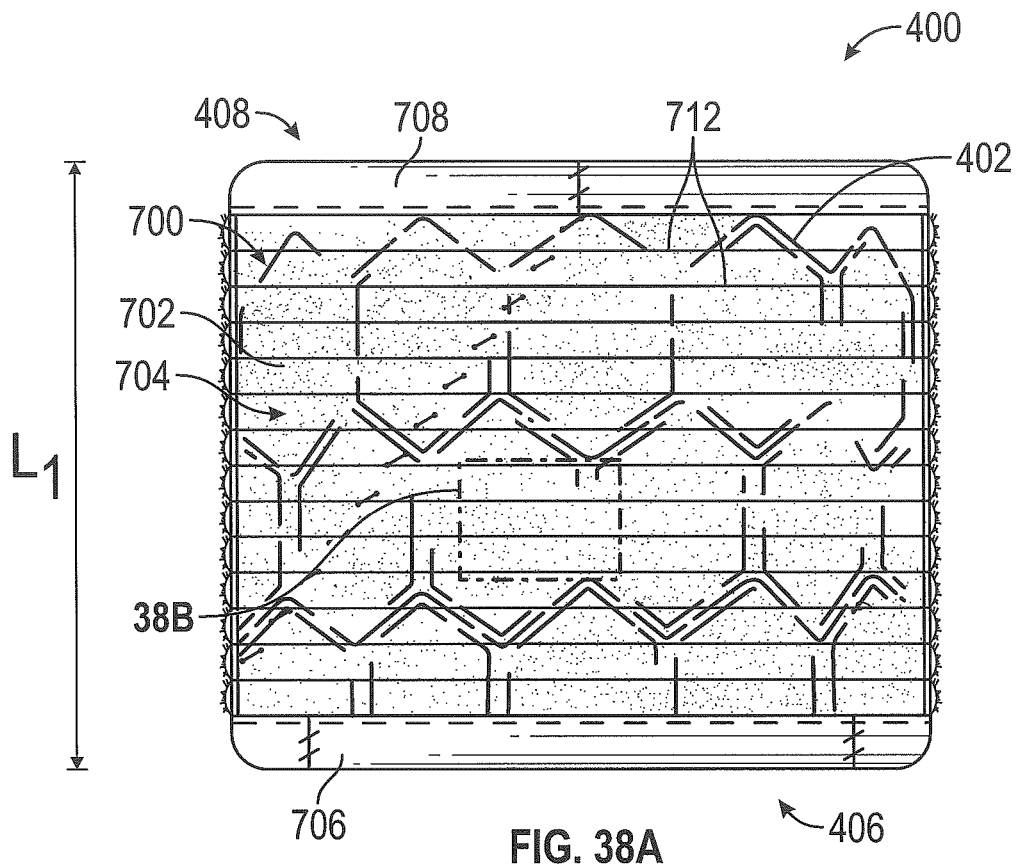
FIG. 38A is a side elevation view of the prosthetic valve of FIG. 19 including an outer covering, according to another embodiment.
Figure 38B:
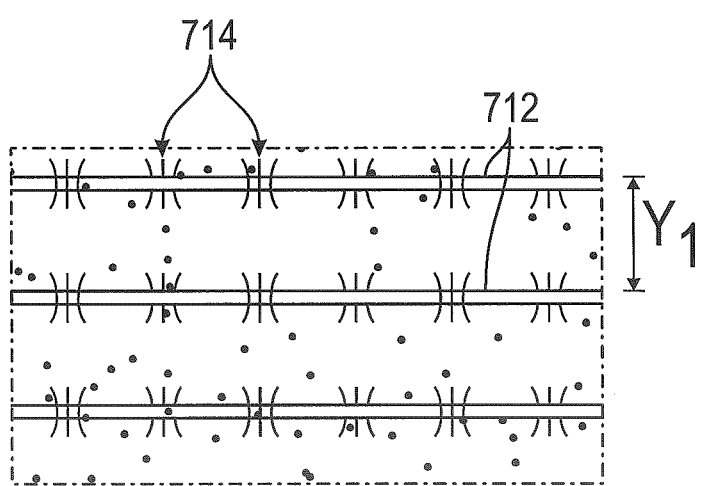
FIG. 38B is a detail view of the fabric of the outer covering of FIG. 38A.
Figure 39A:
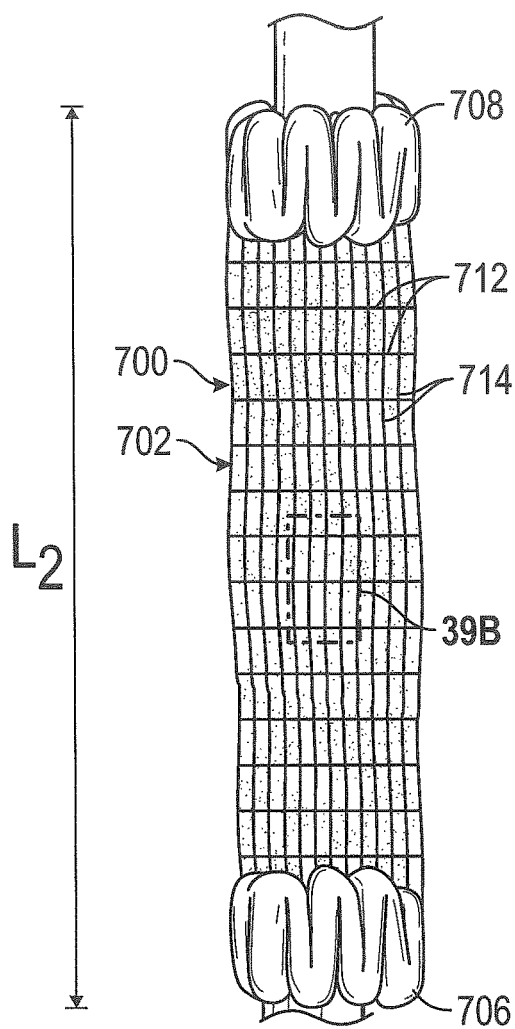
FIG. 39A is a plan view illustrating the prosthetic heart valve of FIG. 38A crimped onto a shaft of a delivery device.
Figure 39B:
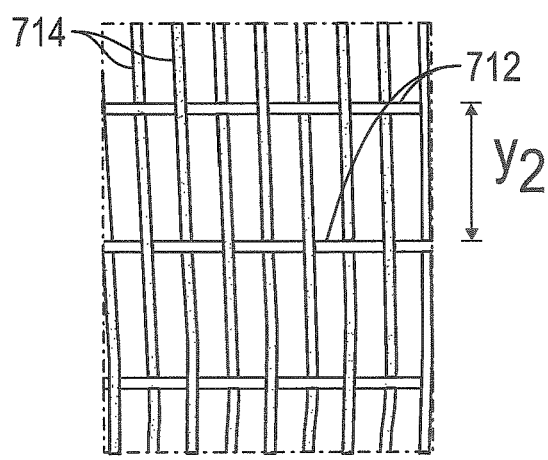
FIG. 39B is a detail view of the outer covering of the prosthetic heart valve in FIG. 39A.

When the fabric is in the relaxed state, the textured filaments 716 of the weft yarns 714 can be widely dispersed such that individual weft yarns are not readily discerned, as in FIGS. 38A and 38B. When tensioned, the filaments 716 of the weft yarns 714 can be drawn together as the weft yarns elongate and the kinks, twists, etc., of the filaments are pulled straight such that the fabric is stretched and the thickness decreases. In certain embodiments, when sufficient tension is applied to the fabric in the axial (e.g., weft) direction, such as when the prosthetic valve is crimped onto a delivery shaft, the textured fibers 716 can be pulled together such that individual weft yarns 714 become discernable, as best shown in FIGS. 39B and 40B.

Thus, for example, when fully stretched, the main layer 702 can have a second thickness $t_3$, as shown in FIG. 40B that is less than the thickness $t_2$. In certain embodiments, the thickness of the tensioned weft yarns 714 may be the same or nearly the same as the thickness $t_1$ of the warp yarns 712. Thus, in certain examples, when stretched the fabric can have a thickness $t_3$ that is the same or nearly the same as three times the thickness $t_1$ of the warp yarns 712 depending upon, for example, the amount of flattening of the weft yarns 714. Accordingly, in the example above in which the warp yarns 712 have a thickness of about 0.06 mm, the thickness of the main layer 702 can vary between about 0.2 mm and about 1.5 mm as the fabric stretches and relaxes. Stated differently, the thickness of the fabric can vary by 750% or more as the fabric stretches and relaxes.

Additionally, as shown in FIG. 40A, the warp yarns 712 can be spaced apart from each other in the fabric by a distance $y_1$ when the outer covering is in a relaxed state. As shown in FIGS. 39B and 40B, when tension is applied to the fabric in the direction perpendicular to the warp yarns 712 and parallel to the weft yarns 714, the distance between the warp yarns 712 can increase as the weft yarns 714 lengthen. In the example illustrated in FIG. 40B, in which the fabric has been stretched such that the weft yarns 714 have lengthened and narrowed to approximately the diameter of the warp yarns 712, the distance between the warp yarns 712 can increase to a new distance $y_2$ that is greater than the distance $y_1$.

In certain embodiments, the distance $y_1$ can be, for example, about 1 mm to about 10 mm, about 2 mm to about 8 mm, or about 3 mm to about 5 mm. In a representative example, the distance $y_1$ can be about 3 mm. In some embodiments, when the fabric is stretched as in FIGS. 39B and 40B, the distance $y_2$ can be about 6 mm to about 10 mm. Thus, in certain embodiments, the length of the outer covering 700 can vary by 100% or more between the relaxed length $L_1$ and the fully stretched length (e.g., $L_2$). The fabric's ability to lengthen in this manner can allow the prosthetic valve to be crimped to diameters of, for example, 23 Fr, without being limited by the outer covering's ability to stretch. Thus, the outer covering 700 can be soft and voluminous when the prosthetic valve is expanded to its functional size, and relatively thin when the prosthetic valve is crimped to minimize the overall crimp profile of the prosthetic valve.

Figure 41A:
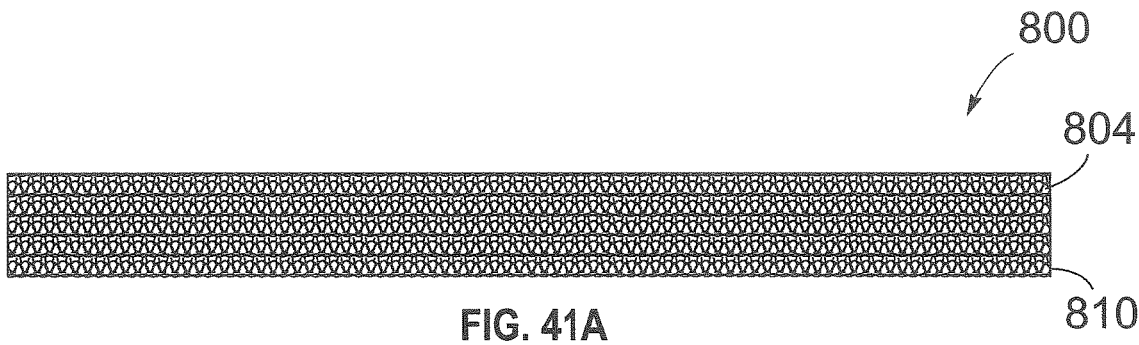
FIG. 41A is a plan view of another embodiment of a fabric outer covering for a prosthetic valve in a laid-flat configuration and including an outer surface defined by a pile layer.
Figure 41B:
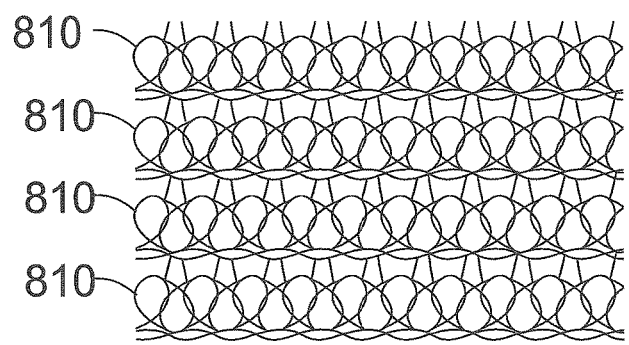
FIG. 41B is a magnified view of the outer covering of FIG. 41A.
Figure 42A:
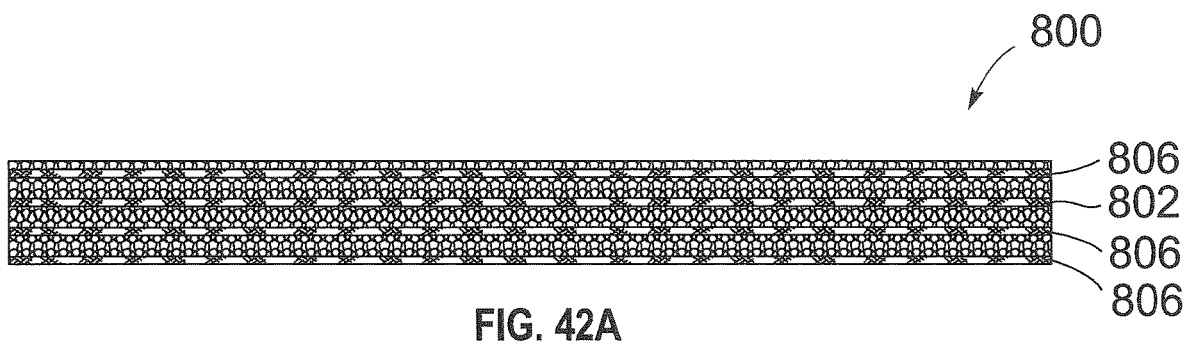
FIG. 42A is a plan view of a base layer of the outer covering of FIG. 41A.
Figure 42B:
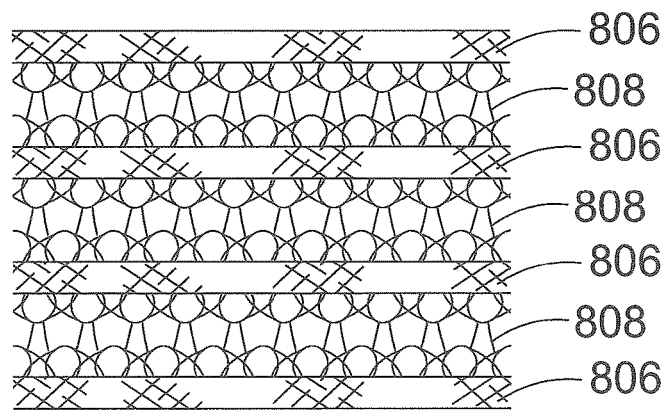
FIG. 42B is a magnified view of the base layer of FIG. 42A.

FIGS. 41A, 41B, 42A, and 42B show an outer sealing member or covering 800 for a prosthetic heart valve (e.g., such as the prosthetic heart valve 400), according to another embodiment. The sealing member 800 can be a dual-layer fabric comprising a base layer 802 and a pile layer 804. FIG. 41A shows the outer surface of the sealing member 800 defined by the pile layer 804. FIG. 42A shows the inner surface of the sealing member 800 defined by the base layer 802. The base layer 802 in the illustrated configuration comprises a mesh weave having circumferentially extending rows or stripes 806 of higher-density mesh portions interspersed with rows or stripes 808 of lower-density mesh portions.

In particular embodiments, the yarn count of yarns extending in the circumferential direction (side-to-side or horizontally in FIGS. 42A and 42B) is greater in the higher-density rows 806 than in the lower-density rows 808. In other embodiments, the yarn count of yarns extending in the circumferential direction and the yarn count of yarns extending in the axial direction (vertically in FIGS. 42A and 42B) is greater in the higher-density rows 806 than in the lower-density rows 808.

The pile layer 804 can be formed from yarns woven into the base layer 802. For example, the pile layer 804 can comprise a velour weave formed from yarns incorporated in the base layer 802. Referring to FIG. 41B, the pile layer 804 can comprise circumferentially extending rows or stripes 810 of pile formed at axially-spaced locations along the height of the sealing member 800 such that there are axial extending gaps between adjacent rows 810. In this manner, the density of the pile layer varies along the height of the sealing member. In alternative embodiments, the pile layer 804 can be formed without gaps between adjacent rows of pile, but the pile layer can comprise circumferentially extending rows or stripes of higher-density pile interspersed with rows or stripes of lower-density pile.

In alternative embodiments, the base layer 802 can comprise a uniform mesh weave (the density of the weave pattern is uniform) and the pile layer 804 has a varying density.

In alternative embodiments, the density of the sealing member 800 can vary along the circumference of the sealing member. For example, the pile layer 804 can comprise a plurality of axially-extending, circumferentially-spaced, rows of pile yarns, or alternatively, alternating axially-extending rows of higher-density pile interspersed with axially-extending rows of lower-density pile. Similarly, the base layer 802 can comprise a plurality axially-extending rows of higher-density mesh interspersed with rows of lower-density mesh.

In other embodiments, the sealing member 800 can include a base layer 802 and/or a pile layer 804 that varies in density along the circumference of the sealing member and along the height of the sealing member.

Varying the density of the pile layer 804 and/or the base layer 802 along the height and/or the circumference of the sealing member 800 is advantageous in that it reduces the bulkiness of the sealing member in the radially collapsed state and therefore reduces the overall crimp profile of the prosthetic heart valve.

In certain embodiments, the outer covering 800 can include inflow and/or outflow protective portions similar to the protective portions 416 and 418 above. However, in other embodiments, the outer covering 800 need not include protective portions and can extend between the top and bottom row of strut members of a frame, or between intermediate rows of strut members, depending upon the particular application.

Although the prosthetic valve covering embodiments described herein are presented in the context of mitral valve repair, it should be understood that the disclosed coverings can be used in combination with any of various prosthetic heart valves for implantation at any of the valves in the heart. For example, the prosthetic valve coverings described herein can be used in combination with transcatheter heart valves, surgical heart valves, minimally-invasive heart valves, etc. The covering embodiments can be used in valves intended for implantation at any of the native annuluses of the heart (e.g., the aortic, pulmonary, mitral, and tricuspid annuluses), and include valves that are intended for implantation within existing prosthetics valves (so called "valve-in-valve" procedures). The covering embodiments can also be used in combination with other types of devices implantable within other body lumens outside of the heart, or heart valves that are implantable within the heart at locations other than the native valves, such as trans-atrial or trans-ventricle septum valves.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

What is claimed is:

1. A prosthetic heart valve, comprising:
  a frame comprising a plurality of strut members, and having an inflow end and an outflow end;
  a leaflet structure situated at least partially within the frame; and
  a covering disposed around an exterior of the frame, the covering comprising:
    a cushioning layer;
    a first strip member folded over an inflow circumferential edge portion of the cushioning layer to form a first protective portion; and
    a second strip member folded over an outflow circumferential edge portion of the cushioning layer to form a second protective portion;
  wherein the first strip member and the second strip member are spaced apart from each other along a longitudinal axis of the prosthetic heart valve; and
  wherein the first strip member comprises a first circumferential edge portion on the outside of the frame and a second circumferential edge portion on the inside of the frame, and the first and second circumferential edge portions are sutured together through the frame.

2. The prosthetic heart valve of claim 1, wherein the cushioning layer forms an exterior surface of the covering.

3. The prosthetic heart valve of claim 1, wherein:
  the cushioning layer comprises a first material; and
  the first strip member comprises a second material different from the first material.

4. The prosthetic heart valve of claim 3, wherein the first material is a woven fabric, and the second material is a polymeric material or a tissue material.

5. The prosthetic heart valve of claim 4, wherein the woven fabric of the cushioning layer comprises texturized yarns that provide compressible volume to the woven fabric.

6. The prosthetic heart valve of claim 5, wherein the woven fabric of the cushioning layer is stretchable between a first configuration corresponding to a radially expanded configuration of the prosthetic heart valve and a second configuration corresponding to a radially collapsed configuration of the prosthetic heart valve.

7. The prosthetic heart valve of claim 6, wherein a thickness of the woven fabric of the cushioning layer is greater when the prosthetic heart valve is in the expanded configuration than when the prosthetic heart valve is in the collapsed configuration.

8. The prosthetic heart valve of claim 4, wherein the first material of the cushioning layer comprises woven polyethylene terephthalate (PET) fabric, and the second material of the first strip member comprises expanded polytetrafluoroethylene (ePTFE).

9. The prosthetic heart valve of claim 1, wherein the first strip member extends around a circumference of the inflow end of the frame, and the second strip member extends around a circumference of the outflow end of the frame.

10. The prosthetic heart valve of claim 1, wherein the first strip member extends over inflow apices of the frame, and the second strip member extends over outflow apices of the frame.

11. The prosthetic heart valve of claim 1, wherein the first and second circumferential edge portions of the first strip member are sutured together through the cushioning layer to form the first protective portion.

12. The prosthetic heart valve of claim 11, wherein:
  the prosthetic heart valve further comprises an inner skirt disposed within the frame; and the first strip member is sutured to the inner skirt.

13. The prosthetic heart valve of claim 1, wherein the second strip member comprises a first circumferential edge portion on the outside of the frame and a second circumferential edge portion on the inside of the frame, and the first circumferential edge portion of the second strip member is sutured to the second circumferential edge portion of the second strip member through the frame.

14. A prosthetic heart valve, comprising:
   a frame comprising a plurality of strut members, and having an inflow end and an outflow end;
   a leaflet structure situated at least partially within the frame; and
   a covering disposed around an exterior of the frame, the covering comprising:
   a cushioning layer comprising a first material, the cushioning layer forming an exterior surface of the covering; and
   a first protective portion at the inflow end of the frame, the first protective portion comprising a second material different from the first material; and
   a second protective portion at the outflow end of the frame, the second protective portion comprising the second material;
   wherein the first protective portion comprises first and second circumferential edge portions that are sutured together through an inflow end portion of the cushioning layer, and the second protective portion is sutured to an outflow end portion of the cushioning layer.

15. The prosthetic heart valve of claim 14, wherein the cushioning layer comprises a woven fabric including texturized yarns that provide compressible volume to the woven fabric.

16. The prosthetic heart valve of claim 15, wherein the cushioning layer comprises polyethylene terephthalate (PET).

17. The prosthetic heart valve of claim 14, wherein the first protective portion comprises a first strip member comprising the second material, the first strip member being folded over an inflow circumferential edge portion of the cushioning layer to form the first protective portion.

18. The prosthetic heart valve of claim 17, wherein the second material comprises expanded polytetrafluoroethylene (ePTFE).

19. The prosthetic heart valve of claim 14, wherein the first protective portion and the second protective portion are spaced apart from each other along a longitudinal axis of the prosthetic heart valve.

20. A prosthetic heart valve, comprising:
   a frame comprising a plurality of strut members, and having an inflow end and an outflow end;
   a leaflet structure situated at least partially within the frame; and
   a covering disposed around an exterior of the frame, the covering comprising:
   a cushioning layer comprising a woven fabric;
   a first strip member folded over an inflow circumferential edge portion of the cushioning layer to form a first protective portion, the first strip member comprising expanded polytetrafluoroethylene (ePTFE); and
   a second strip member folded over an outflow circumferential edge portion of the cushioning layer to form a second protective portion, the second strip member comprising ePTFE;
   wherein the first strip member and the second strip member are spaced apart from each other along a longitudinal axis of the prosthetic heart valve; and
   wherein the first strip member comprises a first circumferential edge portion on the outside of the frame and a second circumferential edge portion on the inside of the frame, and the first and second circumferential edge portions are sutured together through the frame.

* * * * *